US009968769B2

(12) United States Patent
Sasayama et al.

(10) Patent No.: US 9,968,769 B2
(45) Date of Patent: May 15, 2018

(54) CONNECTION DEVICE AND BLOOD COMPONENT SEPARATION APPARATUS

(71) Applicant: NIPRO CORPORATION, Osaka (JP)

(72) Inventors: Norihisa Sasayama, Osaka (JP); Yui Hagiwara, Osaka (JP); Naoko Ishihara, Osaka (JP)

(73) Assignee: Nipro Corporation (JP)

( * ) Notice: Subject to any disclaimer, the term of this patent is extended or adjusted under 35 U.S.C. 154(b) by 604 days.

(21) Appl. No.: 14/386,461

(22) PCT Filed: Jan. 29, 2013

(86) PCT No.: PCT/JP2013/051861
§ 371 (c)(1),
(2) Date: Sep. 19, 2014

(87) PCT Pub. No.: WO2013/140858
PCT Pub. Date: Sep. 26, 2013

(65) Prior Publication Data
US 2015/0073356 A1    Mar. 12, 2015

(30) Foreign Application Priority Data

Mar. 23, 2012    (JP) .................. 2012-068208

(51) Int. Cl.
*A61M 5/32*    (2006.01)
*A61M 39/10*    (2006.01)
(Continued)

(52) U.S. Cl.
CPC ........ *A61M 39/10* (2013.01); *A61M 5/31515* (2013.01); *A61M 5/3202* (2013.01);
(Continued)

(58) Field of Classification Search
CPC .. A61M 36/10; A61M 5/3275; A61M 5/3202; A61M 2005/3268; A61M 1/029;
(Continued)

(56) References Cited

U.S. PATENT DOCUMENTS 4,762,516 A    8/1988 Luther et al.
4,832,696 A    5/1989 Luther et al.
(Continued)

FOREIGN PATENT DOCUMENTS

EP    0 281 421    9/1988
EP    2077115 A1    7/2009
(Continued)

OTHER PUBLICATIONS

Marx, Robert E. and Garg, Arun K.; "Dental and Craniofacial Aplications of Platelet-Rich Plasma," Quintessence Publishing Co. 2005 (Abstract and TOC).

*Primary Examiner* — Imani Hayman
*Assistant Examiner* — Leah Swanson
(74) *Attorney, Agent, or Firm* — Jordan and Koda, PLLC

(57) ABSTRACT

To prevent a user from accidentally pricking the user with a hollow needle when separating blood components using a syringe and a connection device. A blood component separation apparatus has three syringes and a connection device. The connection device is attached to one syringe and is inserted into other syringes. The connection device has a first member to which a base end of a hollow needle is joined and a second member which is connected to the first member in such a manner as to be able to move relative to the first member. The second member is moved back and forth between a first position where a tip of the hollow needle is accommodated and a second position where the tip of the hollow needle is exposed. The second member has elastic portions which are elastically deformed in the movement from the first position to the second position. The elastically (Continued)

deformed elastic portions elastically energize the second member at the second position to the first position side with respect to the first member.

11 Claims, 25 Drawing Sheets

(51) Int. Cl.
- *A61M 5/315* (2006.01)
- *A61M 1/02* (2006.01)
- *A61M 5/178* (2006.01)

(52) U.S. Cl.
CPC ........... *A61M 5/3275* (2013.01); *A61M 1/029* (2013.01); *A61M 5/178* (2013.01); *A61M 2005/3268* (2013.01)

(58) Field of Classification Search
CPC .. A61M 5/321; A61M 5/3213; A61M 5/3246; A61M 5/3257; A61M 5/3271; A61M 5/3272; A61M 5/3273; A61M 2005/3247; A61M 2005/3258; A61M 2005/3267
See application file for complete search history.

(56) References Cited

U.S. PATENT DOCUMENTS

| | | |
|---|---|---|
| 6,171,284 B1 | 1/2001 | Kao et al. |
| 9,050,403 B2 | 6/2015 | Morimoto et al. |
| 2004/0267210 A1 | 12/2004 | Popovsky |
| 2009/0299295 A1 | 12/2009 | Rubnistein et al. |
| 2010/0025342 A1 | 2/2010 | Morimoto et al. |

FOREIGN PATENT DOCUMENTS

| | | | |
|---|---|---|---|
| JP | 63-229062 | 9/1988 | |
| JP | 2005-278910 | 10/2005 | |
| JP | 2005-536248 | 12/2005 | |
| JP | 2006-232834 | 9/2006 | |
| JP | 2008-110272 | 5/2008 | |
| WO | WO-2008/050688 | 5/2008 | |
| WO | WO-2009046560 A2 | 4/2009 | |
| WO | WO 2011092518 A2 * | 8/2011 | ............ A61M 5/326 |
| WO | WO 2012000836 A1 * | 1/2012 | ............ A61M 5/326 |

* cited by examiner (A)

(B)

(C)

CONNECTION DEVICE AND BLOOD COMPONENT SEPARATION APPARATUS

BACKGROUND OF THE INVENTION

The present invention relates to a connection device for use in a blood component separation apparatus which obtains components, such as platelet rich plasma, from blood by centrifugal separation and a blood component separation apparatus having the connection device.

BACKGROUND ART

In the whole blood containing blood components, red blood cells, white blood cells, and blood platelets are separated to be used for raw materials of blood products, medical treatment, and the like. Platelet rich plasma (PRP) which is plasma containing a large number of blood platelets may be separated to be used. The whole blood containing blood cell components contains about 95% of red blood cells, 3% of white blood cells, and about 1% blood platelets. In contrast thereto, the platelet rich plasma contains blood platelets in a high proportion. The proportion of the blood platelets in the platelet rich plasma is not particularly defined. In general, when considering that the proportion of the plasma in the whole blood is about 55%, the proportion of the blood platelets contained in the plasma from which the blood cell components are removed is considered to be about 2%. The platelet rich plasma contains blood platelets in a proportion clearly higher than about 2%.

It is known that growth factors, such as PDGF, TGF-β, and ILGF, are present in a-granules of the blood platelets. The fact that these growth factors play an effective role in healing of wounds and organization regeneration has drawn attention. For example, the utilization of the platelet rich plasma has been expected in regeneration medicine, such as a periodontium regeneration method (Patent Literature 1, Patent Literature 2, and Non-patent Literature 1).

Patent Literature 3 discloses a syringe for obtaining the platelet rich plasma. The syringe has a syringe barrel in which a blood collection needle and a cap are attached to and detached from a port, a gasket disposed in the internal space of the syringe barrel, and a plunger which can be attached to and detached from the gasket.

When obtaining the platelet rich plasma, first, the blood collection needle is attached to the syringe barrel and also the plunger is attached to the gasket, and then blood is collected. After the blood collection, the blood collection needle is removed, and then the cap is attached. In this process, the plunger is removed from the gasket, as required. In this state, the syringe barrel is attached to a centrifuge, and then weak centrifugation is performed. The whole blood is separated by the weak centrifugation into a red blood cells division in the lower side and plasma containing white blood cells and blood platelets in the upper side. Next, the plunger is attached to the gasket and also the cap is removed, and then the red blood cells division in the lower side is discharged from the syringe barrel. Thereafter, the cap is attached. In this process, the plunger is removed from the gasket, as required. In this state, the syringe barrel is attached to a centrifuge, and then strong centrifugation is performed. The plasma is separated by the strong centrifugation into platelet rich plasma in the lower side and a supernatant in the upper side. Then, the plunger is attached and also the cap is removed, and then the platelet rich plasma is discharged from the syringe to obtain the platelet rich plasma.

The blood component separation apparatus having the syringe of this kind includes one which sucks plasma and a supernatant from a syringe barrel using another syringe having the same configuration instead of discharging a red blood cells division and platelet rich plasma from a syringe barrel, and then obtains platelet rich plasma. In such a blood component separation apparatus, a hollow needle and a connection device are attached to and detached from the syringe which sucks the plasma and the supernatant. The hollow needle penetrates a gasket of the syringe subjected to the suction is brought into contact with the plasma and the supernatant. The connection device is moved by pressing the gasket of the syringe subjected to the suction.

CITATION LIST

[Patent Literature 1] Japanese Patent Laid-Open No. 2006-232834
[Patent Literature 2] Japanese Patent Laid-Open No. 2005-278910
[Patent Literature 3] Japanese Patent Laid-Open No. 2008-110272
[Non Patent Literature 1] Application of platelet rich plasma to mouth, Written by Robert E. Marcus, Published by Quintessence Publishing Co., Ltd.

SUMMARY OF INVENTION

When the blood component separation apparatus described above is used, there is a possibility that a user may accidentally prick a finger or the like with the hollow needle. As a result, there is a problem that the user may be injured or may be infected from blood.

The present invention has been made in view of the problems described above and aims at providing a means of preventing a user from accidentally pricking the user with a hollow needle in the use of the blood component separation apparatus.

(1) A connection device of the present invention has a first member in a tube shape having a first internal space which extends in the longitudinal direction and opens to both end sides, a hollow needle having a hub connectable to a port of a syringe provided on the base end side of the first member and extending from the hub to the tip side in the first internal space of the first member, and a second member which has a second internal space which extends in the longitudinal direction and opens to both end sides, which is provided on the tip side of the first member by continuously connecting the second internal space to the first internal space, and which can move relative to the first member in the longitudinal direction. The second member can move to a first position where the tip of the hollow needle is accommodated in the second internal space and a second position where the tip of the hollow needle is exposed from the second internal space and is elastically energized to the first position side relative to the first member.

The syringe filled with the whole blood by blood collection is centrifuged in the state where the plunger is removed, for example, whereby the whole blood is separated into a blood cell component and plasma. The hub of the connection device is attached to a port of a syringe for extracting the plasma from the syringe. In the connection device, the second member is elastically energized to the first position side. Therefore, when the connection device is attached to the syringe, the tip side of the hollow needle is accommodated in the second internal space of the second member.

The connection device attached to the syringe is inserted into the syringe, in which the centrifugal separation is performed, from the tip side of the second member. When the second member abuts on the gasket in the syringe to be further pressed, the second member moves to the second position from the first position against the energization force. Thus, the tip of the hollow needle is exposed from the second internal space of the second member, so that the hollow needle penetrates the gasket. The tip of the hollow needle which penetrates the gasket contacts the plasma in the syringe. Therefore, when the plunger is operated in the syringe to which the connection device is attached, the plasma is extracted through the hollow needle. After the plasma is extracted, the hollow needle is removed from the gasket. Then, when the second member is separated from the gasket, the second member moves to the first position from the second position by the energization force. Thus, the tip side of the hollow needle is accommodated again in the second internal space of the second member.

(2) The connection device may be configured so that the first member is provided with lock mechanisms which fix the second member in such a manner that the second member does not move from the first position. In the connection device after use, the second member is fixed to the first position by the lock mechanisms. Thus, when the connection device after use is handled, a user does not contact the hollow needle.

(3) The connection device may be configured so that tapered inclines which outwardly spread toward the base end side are provided on the outer wall on the tip side of the first member, the second member is provided with projection pieces which are extended in the longitudinal direction toward the inclines and can be elastically deformed in such a manner as to outwardly spread by abutting of the tip side on the inclines, and the second member is elastically energized to the first position side by restoring force of the elastically deformed projection pieces. Thus, the second member can be elastically energized to the first position side with a simple configuration.

(4) The connection device may be configured so that engagement portions with which the tip side of the projection pieces can engage are provided on the tip side of the inclines of the first member, and the second member is fixed to the first position by engagement of the projection pieces with the engagement portions. Thus, the lock mechanism is achieved with a simple configuration.

(5) The connection device may be configured so that long holes which extend in the longitudinal direction are formed in the outer wall on the tip side of the first member, the second member is provided in such a manner that the tip side can move into/out of the first internal space of the first member, in which elastic pieces extended from the base end side are extended to the outside of the first member through the long holes, and are elastically deformed to be connected to the tip side of the first member, and the second member is elastically energized to the first position side by restoring force of the elastically deformed elastic pieces. Thus, the second member can be elastically energized to the first position side with a simple configuration.

(6) The connection device may be configured so that engagement portions with which the elastic pieces can engage are provided in the long holes of the first member and the second member is fixed to the first position by engagement of the elastic pieces with the engagement portions. Thus, the lock mechanism is realized with a simple configuration.

(7) The connection device may be configured so that tapered inclines which outwardly spread toward the tip side are provided on the outer wall on the base end side of the second member, the first member is provided with projection pieces which are extended toward the inclines in the longitudinal direction and can be elastically deformed in such a manner as to outwardly spread by abutting of the tip side on the inclines, and the second member is elastically energized to the first position side by restoring force of the elastically deformed projection pieces. Thus, the second member can be elastically energized to the first position side with a simple configuration.

(8) The connection device may be configured so that engagement concave portions are provided in the outer wall of the first member, and the second member is provided with engagement convex portions which can engage with the engagement concave portions, energizing portions which elastically energize the engagement convex portions to a side where the engagement convex portions do not engage with the engagement concave portions, and lock portions which fix the engagement convex portions to a position where the engagement convex portions engage with the engagement concave portions against energization force caused by the energizing portions, in which the second member is fixed to the first position by engagement of the engagement concave portions engage with the engagement convex portions. Thus, the lock mechanism is achieved with a simple configuration.

(9) As one example, the second member is provided with holding portions which support the engagement convex portions facing the engagement concave portions, a pair of the energizing portions are provided on both sides of the holding portions and elastically support the holding portions by the pair of energizing portions, and the lock portions are projected toward both the pair of energizing portions from the engagement convex portions and engage with both the pair of energizing portions to thereby fix the engagement convex portions to the position where the engagement convex portions engage with the engagement concave portions.

(10) As another example, the second member is provided with holding portions which support the engagement convex portions facing the engagement concave portions, a pair of the energizing portions are provided on both sides of the holding portions and elastically support the holding portions by one of the pair of energizing portions, and the lock portions are projected toward the other one of the pair of energizing portions from the engagement convex portions and engage with the other end of the energizing portions to thereby fix the engagement convex portions to the position where the engagement convex portions engage with the engagement concave portions.

(11) The present invention can also be regarded as a blood component separation apparatus having a connection device, a first syringe having a first syringe barrel into which the tip side of the connection device is inserted, a first gasket which is moved back and forth in the first syringe barrel, and a plunger which is attached to and detached from the first gasket, a cap which seals a first port of the first syringe barrel, and a second syringe having a second port to which the connection device is attached, in which when the second member of the connection device reaches a second position, the hollow needle exposed from the second internal space can penetrate the first gasket.

According to the present invention, the hollow needle is accommodated in the second member in the state where the connection device is inserted into the syringe and does not abut on the gasket. Therefore, a user is prevented from accidentally touching the hollow needle or pricking the user with the hollow needle.

DESCRIPTION OF THE PREFERRED EMBODIMENTS

Hereinafter, a preferable embodiment of the present invention is described. This embodiment is merely one embodiment of the present invention and it is a matter of course that the embodiment can be modified insofar as the scope of the present invention is not altered.

[Outline of Blood Component Separation Apparatus 10]

Figure 1:
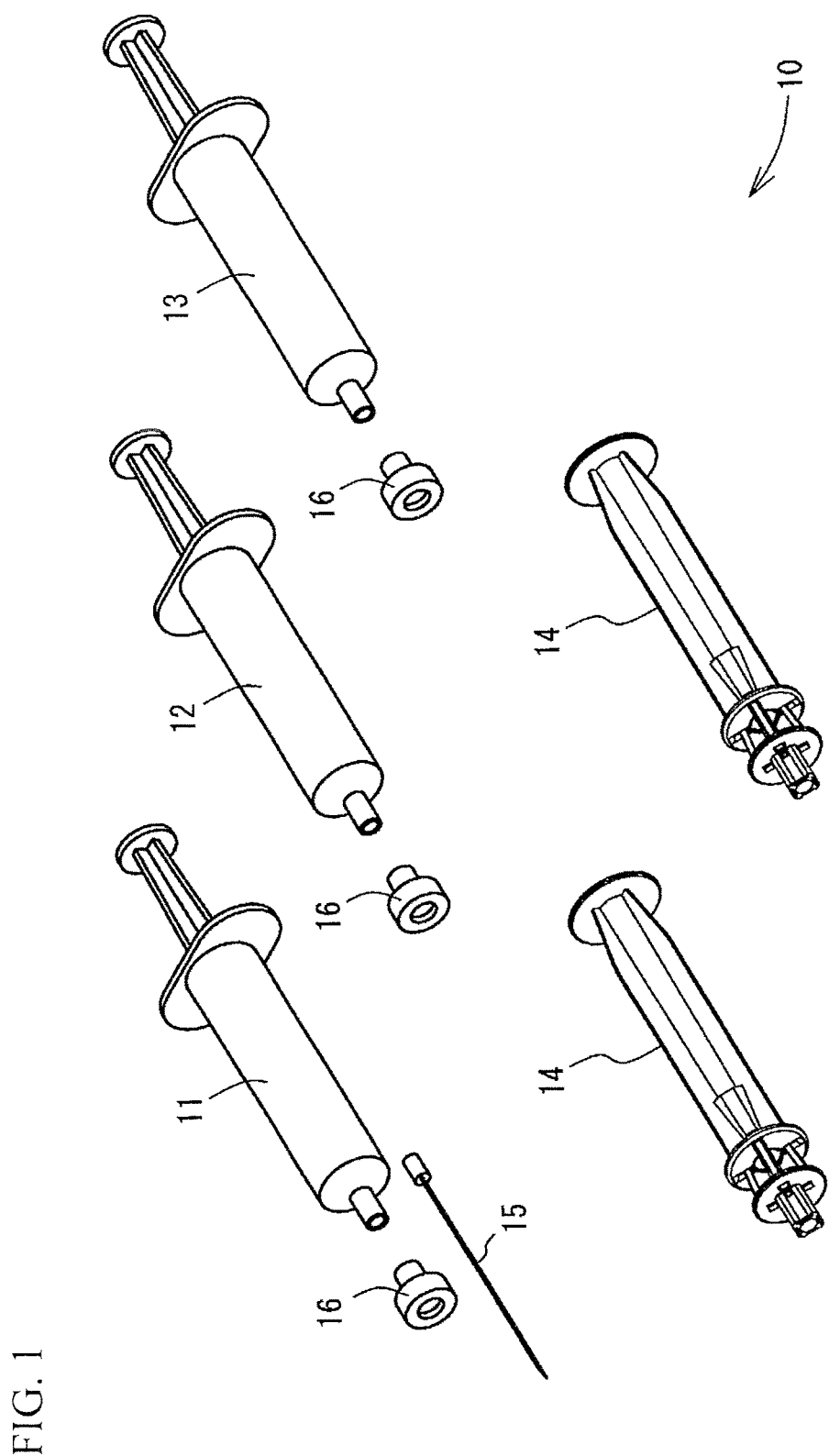
FIG. 1 includes perspective views of a blood component separation apparatus 10.

As illustrated in FIG. 1, a blood component separation apparatus 10 has syringes 11, 12, and 13 and two connection devices 14. The syringe 11 is used for blood collection. Moreover, the syringe 11 is used for weak centrifugation of blood (whole blood) obtained by blood collection. The syringe 12 and one connection device 14 are used for sucking a centrifuged division 55 (FIG. 9(B)) separated by weak centrifugation. Moreover, the syringe 12 is used for strong centrifugation of the sucked centrifuged division 55. The syringe 13 and the other connection device 14 are used for sucking a supernatant 57 (FIG. 9(D)) separated by strong centrifugation. The syringes 11 and 12 are equivalent to a first syringe. The syringes 12 and 13 are equivalent to a second syringe. Since the syringes 11, 12, and 13 have the same configuration, the syringe 11 is described below.

Figure 2:
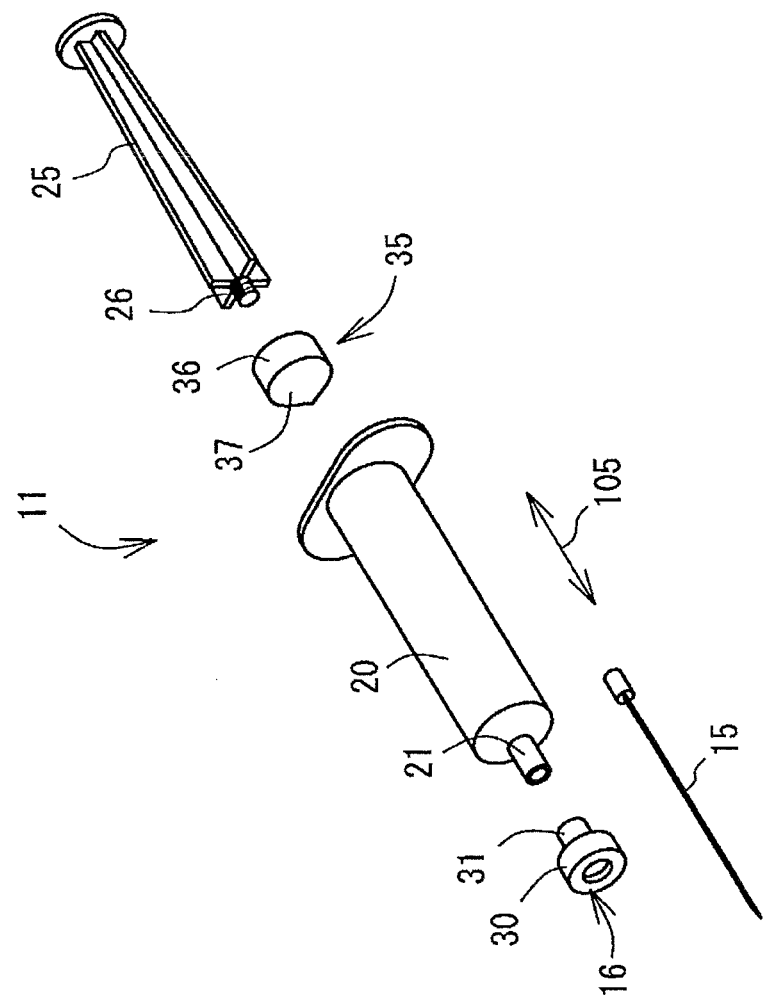
FIG. 2 is an exploded perspective view of a syringe 11.

As illustrated in FIG. 2, the syringe 11 has a syringe barrel 20, a blood collection needle 15, a cap 16, a gasket 35, and a plunger 25.

Figure 3:
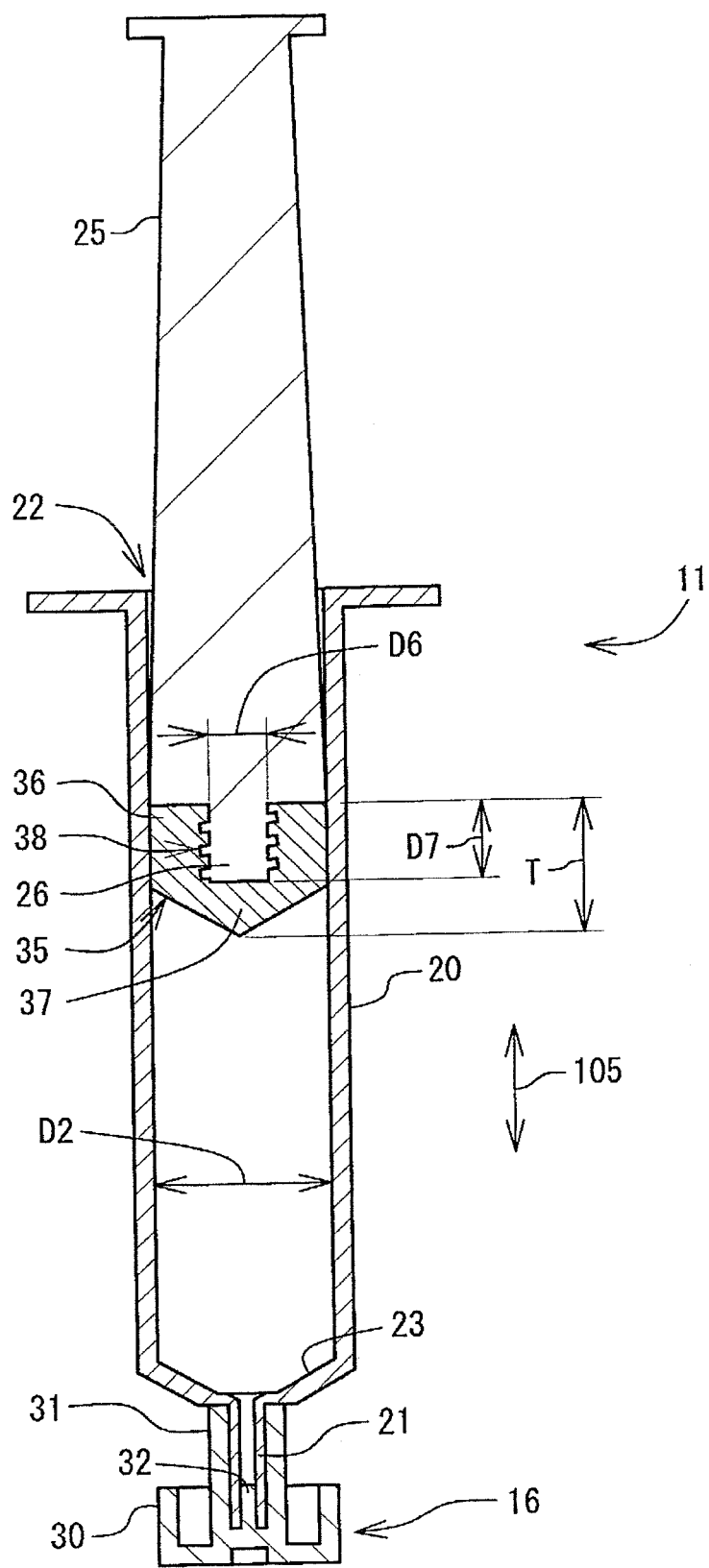
FIG. 3 is a longitudinal sectional view of the syringe 11 in the state where a cap 16 is attached thereto.

The syringe barrel 20 has a cylindrical shape. The diameter of one end in a longitudinal direction 105 (direction along the central axis line) of the syringe barrel 20 is reduced, whereby a port 21 to/from which the blood collection needle 15 and the cap 16 are attached and detached is constituted. As illustrated in FIG. 3, the diameter of the other end of the syringe barrel 20 is not reduced and opens. The gasket 35 is inserted from an opening 22 of the syringe barrel 20.

The gasket 35 has a columnar portion 36 on the side of the opening 22 and a cone portion 37 on the side of the port 21. The columnar portion 36 has a columnar shape whose outer diameter is almost the same as the internal diameter of the syringe barrel 20 and is stuck to the inner circumferential surface of the syringe barrel. 20 over the entire circumference. The gasket 35 seals the internal space of the syringe barrel 20 in a fluid-tight manner. The cone portion 37 is formed into a conical shape according to the shape of a bottom surface 23 in such a manner as to be able to be stuck to the bottom surface 23 of the syringe barrel 20. The cone portion 37 is stuck to the bottom surface 23 of the syringe barrel 20 when the gasket 35 is deeply pressed into the syringe barrel 20. Thus, mixing of the air into the collected blood, the sucked centrifuged division 55, and the sucked supernatant 57 (FIG. 9) is suppressed.

Moreover, the gasket 35 has a screw hole 38 into which a screw portion 26 of the plunger 25 is screwed.

As illustrated in FIG. 2, the plunger 25 is a rod-shape member and has the screw portion 26, which is screwed into the screw hole 38 of the gasket 35, on one end portion in the axial direction. The plunger 25 is inserted into the syringe barrel 20 from the side of the screw portion 26 to be attached to the gasket 35. The plunger 25 is attached to the syringes 11, 12, and 13 in blood collection and sucking of the centrifuged division 55 and the supernatant 57 (FIG. 9) and is removed from the syringes 11 and 12 in centrifugal separation. A user operates the plunger 25 to cause the gasket 35 to move back and forth along the longitudinal direction 105.

As illustrated in FIG. 3, the cap 16 has a large diameter portion 30, a small diameter portion 31 disposed inside the large diameter portion 30, and a plug portion 32 disposed inside the small diameter portion 31. When the cap 16 is attached to the port 21, the inner circumferential surface of the small diameter portion 31 is stuck to the outer circumferential surface of the port 21 over the entire circumference. The plug portion 32 enters the internal space of the port 21 to block the internal space. The cap 16 is attached to the syringe barrel 20 in centrifugal separation and the like.

Glass, resin materials, and the like can be used for the raw materials of the syringe barrel 20, the gasket 35, the plunger 25, and the cap 16. When considering that the blood component separation apparatus 10 is treated as a disposal article and is sterilized, it is common to form the syringe barrel 20 and the plunger 25 with a molded article of polypropylene, to form the cap 16 with a molded article of polypropylene or elastomer, and to form the gasket 35 with a molded article of elastomer.

[Connection Device 14]

Figure 4:
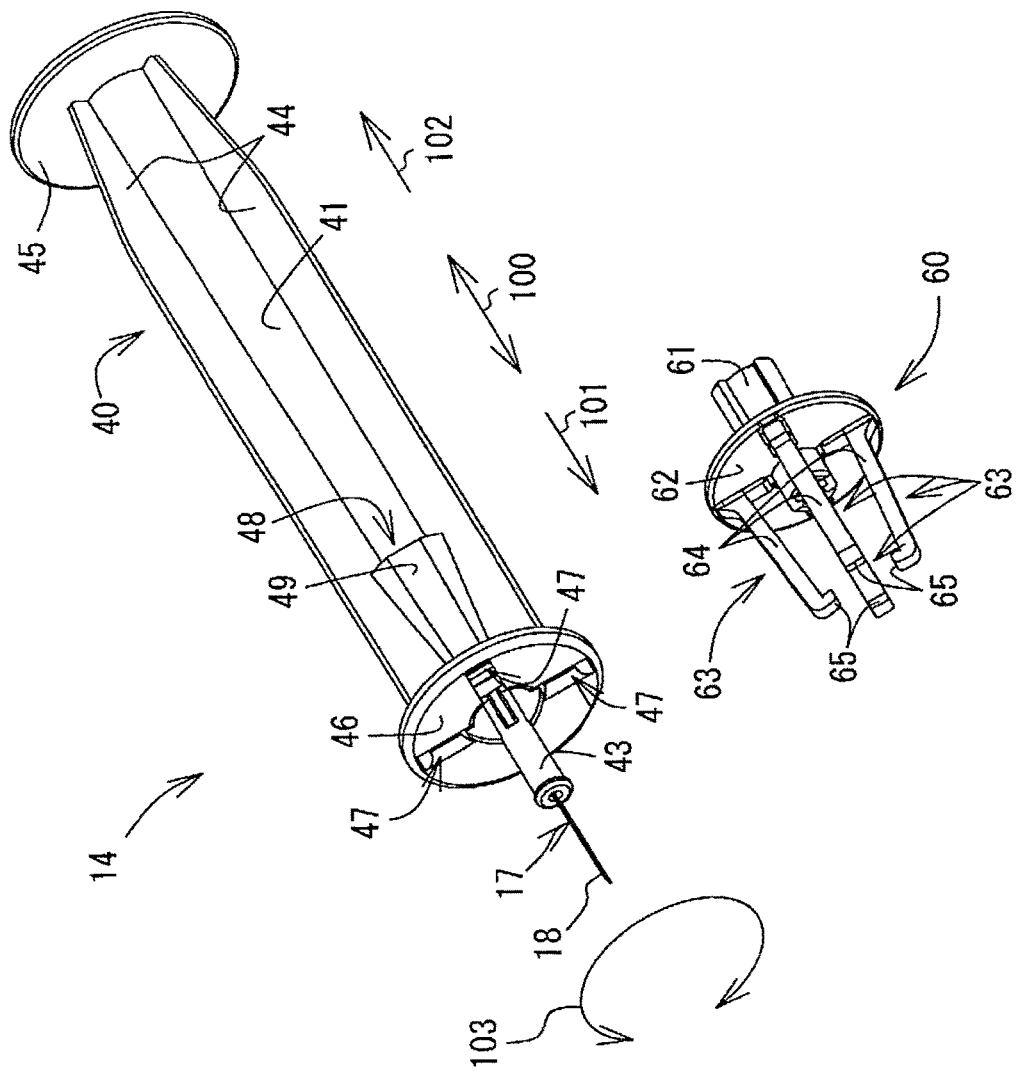
FIG. 4 is an exploded perspective view of a connection device 14.
Figure 5:
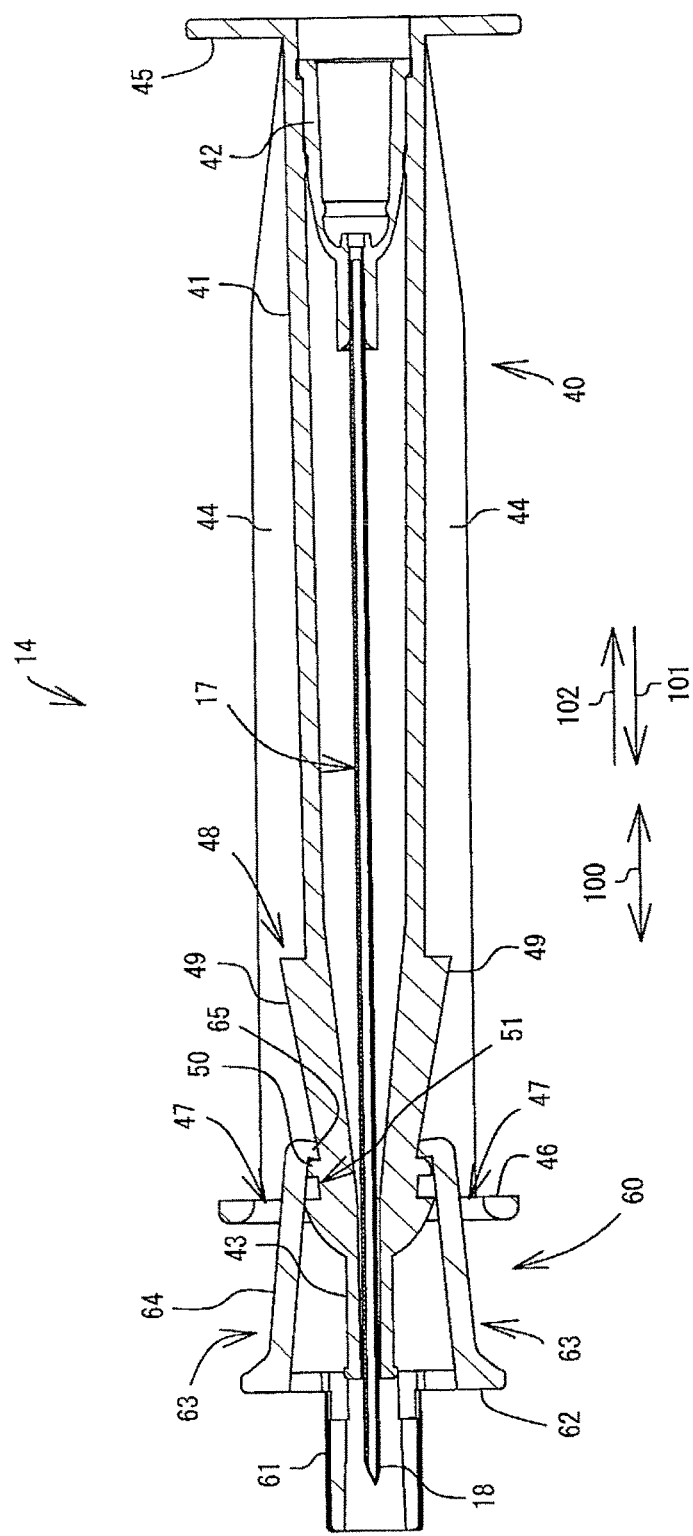
FIG. 5 is a longitudinal sectional view of the connection device 14.
Figure 9:
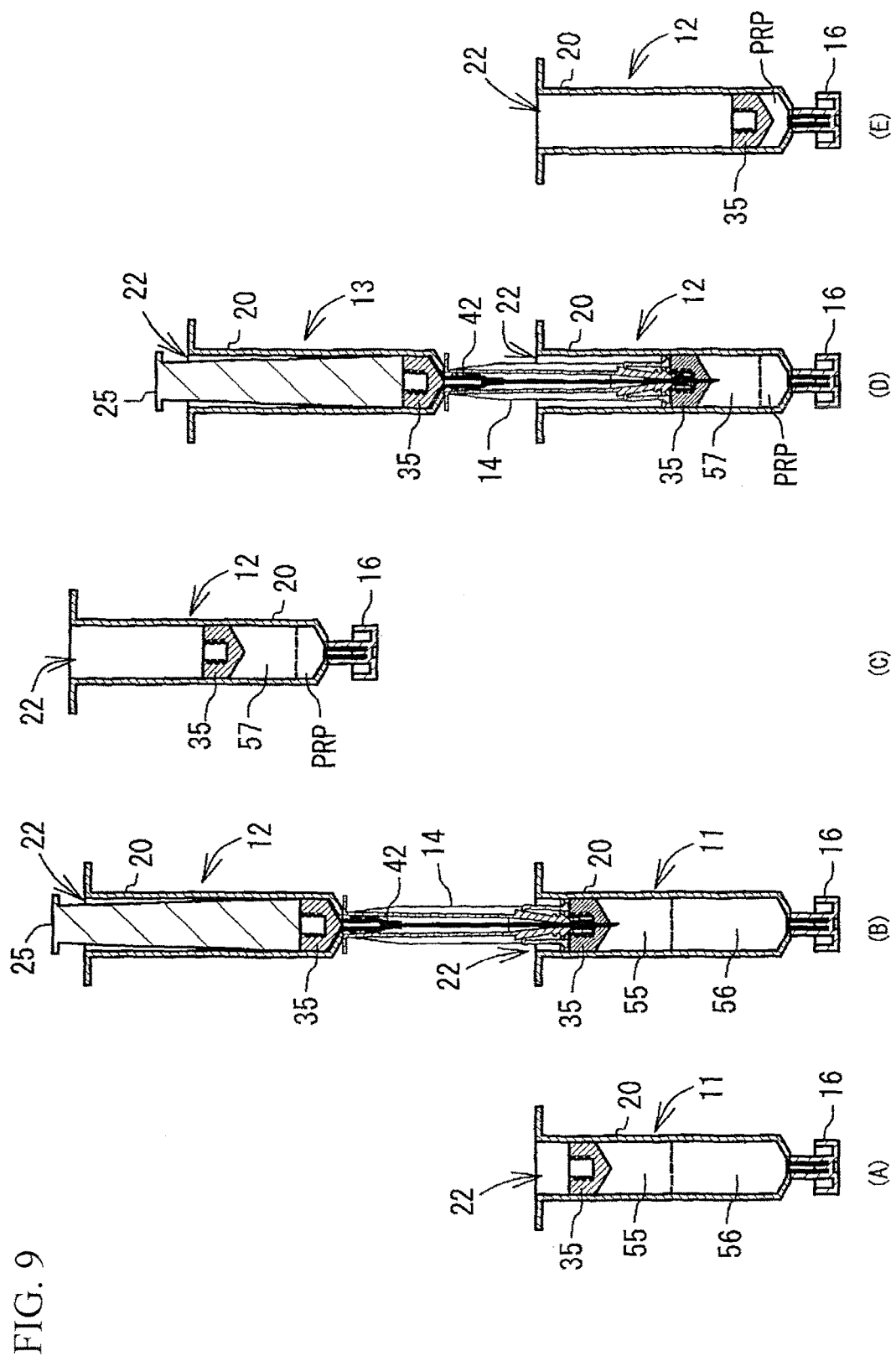
FIG. 9 includes views explaining a procedure of using the blood component separation apparatus 10.

As illustrated in FIG. 9, the connection device 14 is attached to the syringes 12 and 13 for use when sucking the centrifuged division 55 and the supernatant 57. As illustrated in FIG. 4, the connection device 14 has a first member 40, a second member 60, a hollow needle 17, and a hub 42 (FIG. 5). The first member 40 is a member which holds the hub 42 and the hollow needle 17. The second member 60 is a member which covers a tip 18 of the hollow needle 17.

[First Member 40]

The first member 40 is a resin molded article of polypropylene or the like having a cylindrical base 41, reinforcing ribs 44, a first flange 45, a second flange 46, and a support portion 48. The following description is given while defining a direction parallel to the central axis line of the base 41 as an axial direction 100, one direction of the axial direction 100 as a first direction 101, the other direction as a second direction 102, and the circumferential direction of the base 41 as a circumferential direction 103. The axial direction 100 is equivalent to the longitudinal direction. In FIG. 4, the second member 60 is illustrated to be opposite to the attachment direction to the first member 40 in the axial direction 300 so that the configuration of the second member 60 is clearly illustrated.

Figure 6:
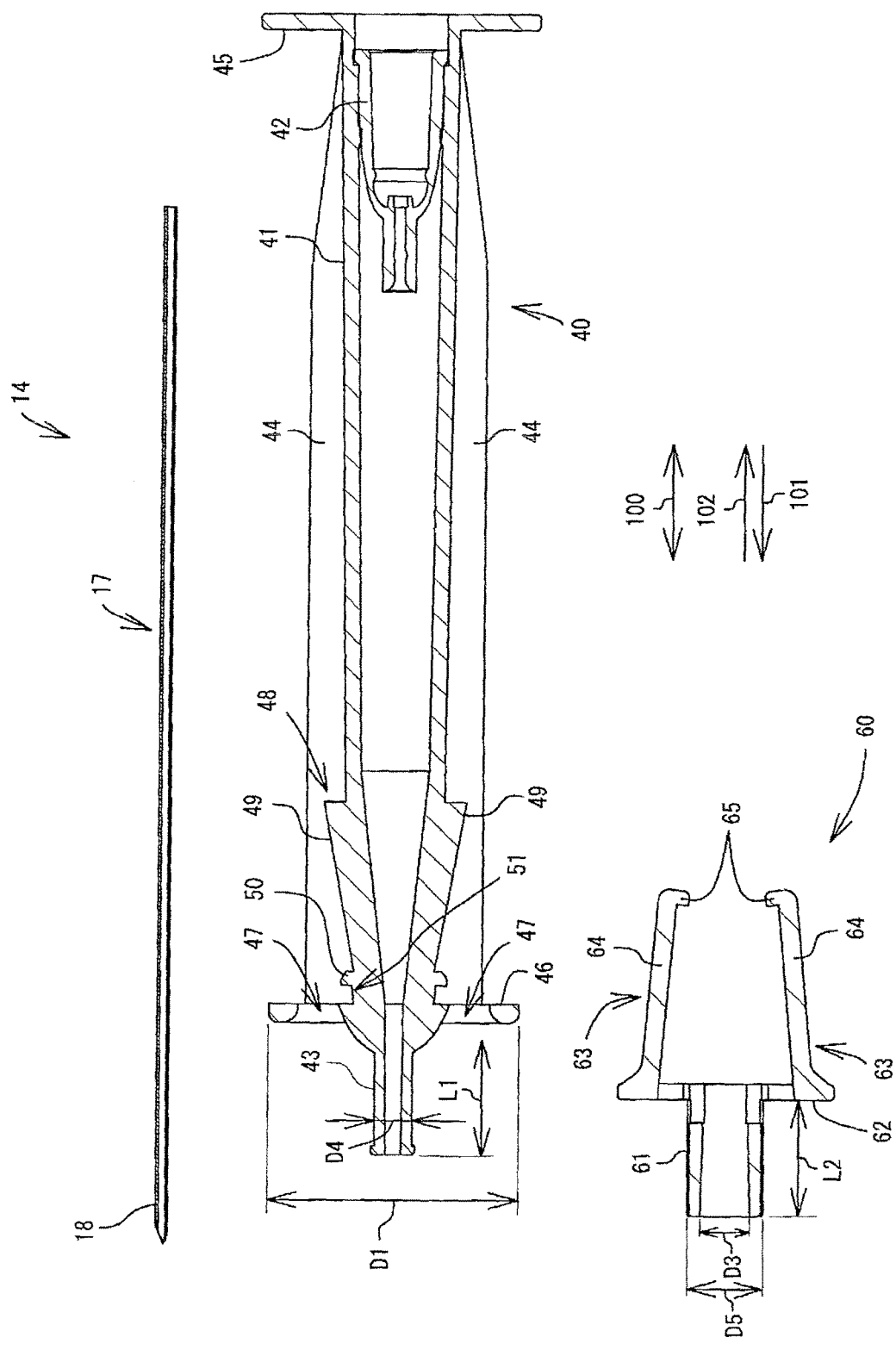
FIG. 6 is an exploded sectional view of the connection device 14.

As illustrated in FIG. 6, the hub 42 is disposed in the internal space (equivalent to the first internal space) on a side in the second direction 102 of the base 41. The hub 42 is a member into the internal space of which the port 21 (FIG. 2) of the syringe barrel 20 is press-fitted. The connection device 14 is attached to and detached from the syringes 12 and 13 through the hub 42.

Figure 7:
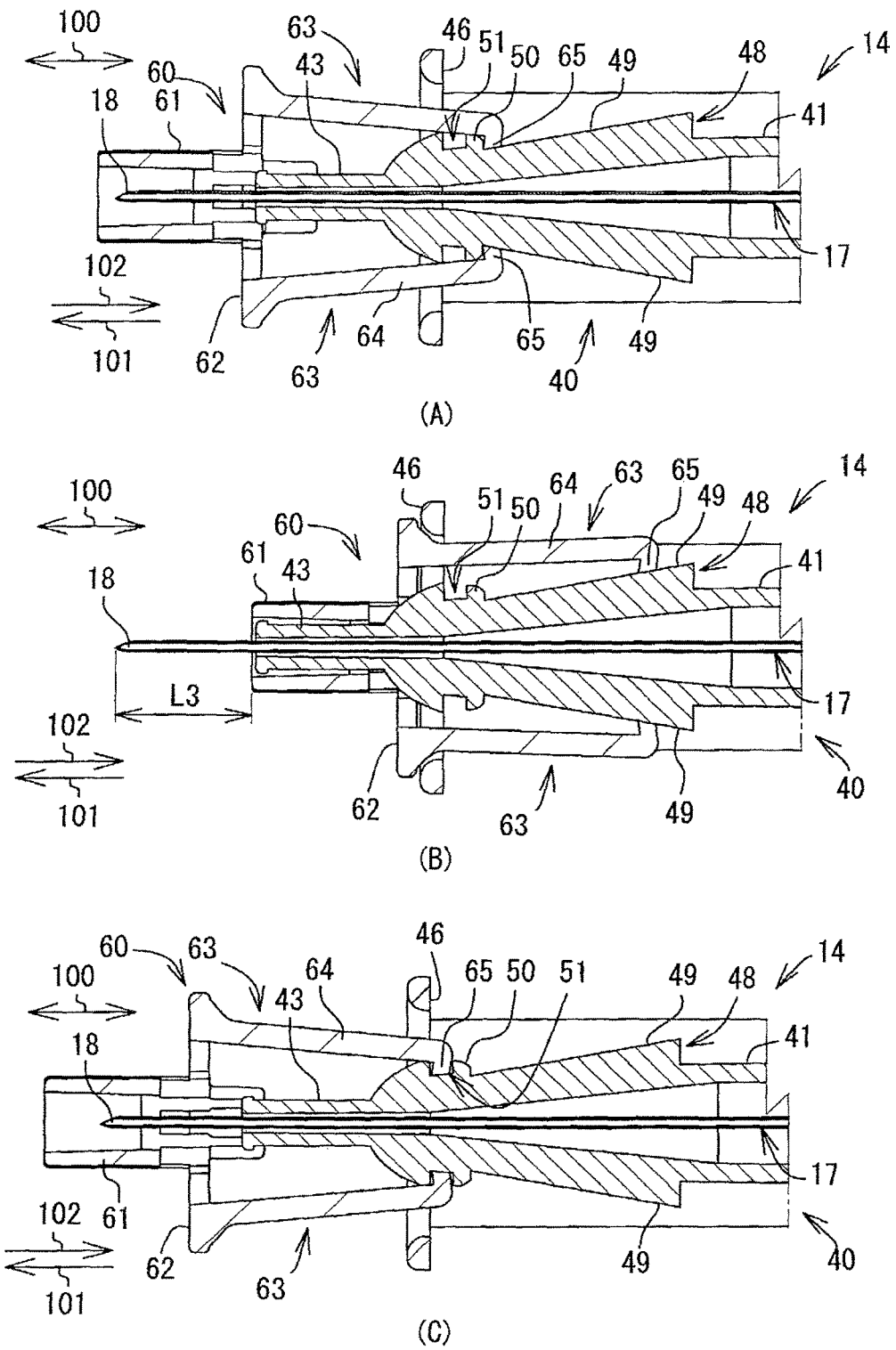
FIG. 7 includes views explaining an operation of the connection device 14.

The diameter of an end portion on a side in the first direction 101 of the base 41 is further reduced than that of the other portions, whereby a small diameter portion 43 is constituted. As illustrated in FIG. 7, the small diameter portion 43 moves into/oat of the internal space of the cylinder portion 61 of the second member 60 in relative movement in the axial direction 100 of the first member 40 and the second member 60 and guides the second member 60 in the axial direction 100.

As illustrated in FIG. 4, the first flange 45 has a disk shape and is projected toward the outside from the outer circumferential surface of an end portion on a side in the second direction 102 of the base 41. For example, a user places a finger on the first flange 45, and then press-fits the port 21 (FIG. 2) of the syringe barrel 20 into the hub 42 (FIG. 5) to attach the connection device 14 to the syringe barrel 20.

Figure 8:
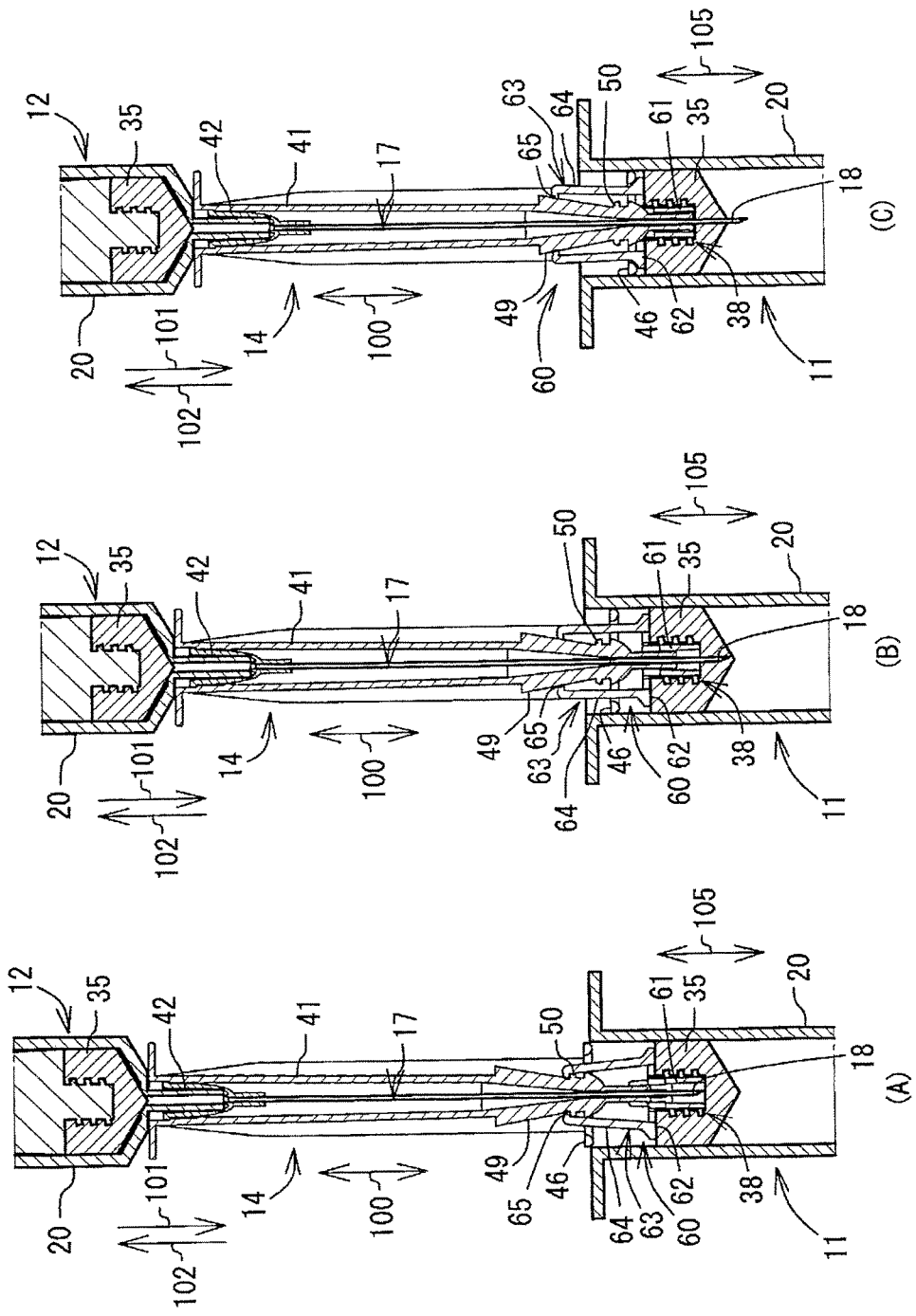
FIG. 8 includes views explaining an operation of the connection device 14 when inserted into a syringe barrel 20.

As illustrated in FIG. 4, the second flange 46 has a disk shape and is projected toward the outside from the outer circumferential surface of the base 41. The second flange 46 is provided on a side in the second direction 102 of the small diameter portion 43. A diameter D1 of the second flange 46 illustrated in FIG. 6 is slightly smaller than an internal diameter D2 (FIG. 3) of the syringe barrel 20. As illustrated in FIG. 8, the second flange 46 guides the connection device 14 in the longitudinal direction 105 of the syringe barrel 20 when the connection device 14 is inserted into the syringe barrel 20.

As illustrated in FIG. 4, the second flange 46 is provided with four insertion holes 47 into which elastic portions 63 of the second member 60 are inserted. The four insertion holes 47 are equally disposed at an interval of 90° in the circumferential direction 103. When the wall surface of the insertion holes 47 and the elastic portions 63 abut on each other in the circumferential direction 103, whirl-stop of the second member 60 in the circumferential direction 103 is performed.

The reinforcing ribs 44 are projected toward the outside from the outer circumferential surface of the base 41, and extend along the axial direction 100. The four reinforcing ribs 44 are provided on the base 41. The four reinforcing ribs 44 are equally disposed at an interval of 90° in the circumferential direction 103. The four reinforcing ribs 44 are shifted by only 45° in the circumferential direction 103 with respect to the insertion holes 47 in such a manner as not to interfere with the elastic portions 63 inserted into the insertion holes 47.

As illustrated in FIG. 6, the distance between the tips of projections of the two reinforcing ribs 44 facing each other in the radial direction of the base 41 is shorter than a diameter D1 of the second flange 46. Therefore, the connection device 14 can be inserted into the syringe barrel 20 as illustrated in FIG. 8.

As illustrated in FIG. 4, the support portion 48 is provided on a side in the second direction 102 of the second flange 46. The support portion 48 elastically deforms the elastic portions 63 of the second member 60 in relative movement in the axial direction 100 of the first member 40 and the second member 60. The support portion 48 has four inclines 49 in a tapered shape which outwardly spread in the second direction 102. The inclines 49 each are provided at a position between the two reinforcing ribs 44 in the circumferential direction 103. As illustrated in FIGS. 7(A) and 7(B), claws 65 of the elastic portions 63 slide on the inclines 49, and projection pieces 64 of the elastic portions 63 are elastically deformed.

As illustrated in FIG. 6, an abutting rib 50 is projected toward the outside in the radial direction of the base 41 from the end on a side in the first direction 101 of the inclines 49. The abutting rib 50 is provided over the entire circumferences of the base 41 in the circumferential direction 103 (FIG. 4). As illustrated in FIG. 7, the abutting rib 50 abuts the claws 65 of the elastic portions 63 which are caused to slide on the inclines 49 to restrain the movement of the second member 60.

As illustrated in FIG. 6, a concave portion 53 which is dented from the outer circumferential surface of the base 41 is provided on a side in the first direction 101 of the abutting rib 50. The concave portion 51 is provided on the entire circumferential surface in the direction 103 (FIG. 4) of the base 41. As illustrated in FIGS. 7(A) and 7(C), when the second member 60 is pulled by a user in the first direction 101, the claws 65 of the elastic portions 63 move beyond the abutting rib 50 to be fitted into the concave portion 51. The second member 60 is fixed to the first member 40 by the fitting of the claws 65 into the concave portion 51. The fixation of the second member 60 is performed when a series of operations for obtaining PRP (FIG. 9) are completed, and then the connection device 14 is discarded. The concave portion 51 is equivalent to the engagement portion and the lock mechanism.

As illustrated in FIG. 6, the surface on a side in the second direction 102 of the abutting rib 50 is formed into a curved surface in such a manner that the claws 65 can move beyond the abutting rib 50. Or, a curved surface may be formed on the claws 65. Moreover, a side in the first direction 101 of the tip of the projection of the abutting rib 50 is edged in such a manner that the claws 65 are not separated from the concave portion 51.

[Hollow Needle 17]

As illustrated in FIG. 5, the hollow needle 17 is disposed at a position overlapping the central axis line of the base 41. The hollow needle 17 is connected to the hub 42 at the base end.

The tip 18 of the hollow needle 17 is projected from the small diameter portion 43 in the first direction 101. A projection amount L3 (FIG. 7(B)) of the hollow needle 17 from the small diameter portion 43 is slightly larger than a thickness T (FIG. 3) of the gasket 35. Thus, as illustrated in FIG. 8(C), the hollow needle 17 can penetrate the gasket 35.

[Second Member 60]

As illustrated in FIG. 4, the second member 60 has a cylinder portion 61, a flange 62, and four elastic portions 63. The second member 60 is a resin molded article molded with polypropylene or the like. Therefore, the elastic portions 63 can be elastically deformed. The second member 60 is attached to the first member 40 by inserting the elastic portions 63 into the insertion holes 47 from the first direction 101 side. Whirl-stop of the second member 60 in the circumferential direction 103 is performed by abutting of the elastic portions 63 on the wall surface of the insertion holes 47 in the circumferential direction 103.

As illustrated in FIG. 6, the internal diameter D3 of the cylinder portion 61 is slightly larger than an outer diameter D4 of the small diameter portion 43. The small diameter portion 43 moves into/out of the cylinder portion 61. Thus, the second member 60 is guided in the axial direction 100. The second member 60 is caused to move back and forth with respect to the first member 40 between a first position illustrated in FIG. 7(A) and a second position illustrated in FIG. 7(B). The internal space of the cylinder portion 61 is equivalent to the second internal space.

As illustrated in FIG. 6, an outer diameter D5 of the cylinder portion 61 is smaller than a diameter D6 (FIG. 3) of the screw hole 38 of the gasket 35. As illustrated in FIG. 8(A), when the connection device 14 is inserted into the syringe barrel 20, the cylinder portion 61 enters the screw hole 38 of the gasket 35.

As illustrated in FIG. 6, a length L2 of the cylinder portion 61 in the axial direction 100 is longer than the projection amount L3 (FIG. 7(B)) of the tip 18 of the hollow needle 17 and is almost the same as a length L1 of the small diameter portion 43 in the axial direction 100. The cylinder portion 61 accommodates the tip 18 of the hollow needle 17 at the first position illustrated in FIG. 7(A), and then covers the small diameter portion 43 at the second position illustrated in FIG. 7(B) to expose the tip 18 of the hollow needle 17. The length L2 is almost the same as a depth D7 (FIG. 3) of the screw hole 38 of the gasket 35. Therefore, as illustrated in FIG. 8(A), when the cylinder portion 61 abuts on the bottom surface of the screw hole 38, the flange 62 and the gasket 35 abut on each other.

As illustrated in FIG. 4, the flange 62 has a disk shape and is projected toward the outside in the radial direction of the cylinder portion 61 from the end on a side in the second direction 102 of the outer circumferential surface of the cylinder portion 61. As illustrated in FIG. 7(B), the flange 62 abuts on the second flange 46 of the first member 40 when the second member 60 reaches the second position. Thus, the movement of the second member 60 beyond the second position is restrained.

As illustrated in FIG. 4, the elastic portions 63 have the four pieces 64 projected from the flange 62 and the claws 65 formed at the tip of the projections of the projection piece 64. The projection pieces 64 are disposed at an interval of 90° in the circumferential direction 103. The projection pieces 64 are inserted into the insertion holes 47 of the second flange 46 of the first member 40.

As illustrated in FIG. 5, the claws 65 are projected toward the inclines 49 of the support portion 48 from the tip portion of the projections of the projection pieces 64 and abut on the inclines 49 at the first position. When the second member 60 is moved to the second position illustrated in FIG. 7(B) from the first position illustrated in FIG. 7(A), the claws 65 slide on the inclines 49, so that the projection pieces 64 are elastically deformed. The elastically deformed projection pieces 64 elastically energize the cylinder portion 61 in the first direction 101 with respect to the first member 40.

[Operation of Connection Device 14]

An operation of the connection device 14 when the connection device 14 is attached to the syringe 12 and is inserted into the syringe barrel 20 of the syringe 11 is described with reference to FIG. 7 and FIG. 8.

As illustrated in FIG. 8, the connection device 14 is attached to the syringe barrel of the syringe 12 through the hub 42. The connection device 14 may be attached to the syringes 12 and 13 beforehand in manufacturing.

As illustrated in FIG. 7(A), before the connection device 14 is inserted into the syringe barrel 20 of the first syringe 11, the tip 18 of the hollow needle 17 is covered with the second member 60.

As illustrated in FIG. 8(A), the connection device 14 is inserted into the syringe barrel 20 of the syringe 11 from the second member 60 side by a user. Thus, the cylinder portion 61 enters the screw hole 38 of the gasket 35 of the syringe 11, and then abuts on the bottom surface of the screw hole 38. When the connection device 14 is further pressed into the syringe barrel 20, the second member 60 is pressed by the gasket 35 to be moved relative to the first member 40 in the second direction 102. Thus, as illustrated in FIG. 8(B), the tip 18 of the hollow needle 17 gradually moves out of the second member 60 to be stuck into the bottom surface of the screw hole 38.

When the second member 60 reaches the second position as illustrated in FIG. 8(C), the tip 18 of the hollow needle 17 penetrates the gasket 35. Thus, the internal space of the syringe barrel 20 of the syringe 11 and the internal space of the syringe barrel 20 of the syringe 12 are made to communicate with each other through the internal space of the hollow needle 17. Moreover, when the second member 60 reaches the second position, the relative movement of the second member 60 to the first member 40 is restrained by abutting of the flange 62 on the second flange 46 of the first member 40. Therefore, when the connection device 14 is further pressed into the syringe barrel 20, the gasket 35 is pressed by the connection device 14 to be moved to the bottom surface 23 (FIG. 3) side of the syringe barrel 20.

When the connection device 14 is inserted into the syringe barrel 20 of the syringe 11, the first member 40 is moved to the second position from the first position, so that the claws 65 of the elastic portions 63 slide on the inclines 49 of the support portion 48 as illustrated in FIGS. 7(A) and 7(B). Thus, the projection pieces 64 are elastically bent. With the elasticity of the bent projection pieces 64, the second member 60 is elastically energized in the first direction 101 with respect to the first member 40.

When the connection device 14 is drawn out from the syringe barrel 20 of the syringe 11 by a user, the second member 60 is moved relative to the first member 40 in the first direction 101 with the elasticity of the projection pieces 64 to be returned to the first position illustrated in FIG. 7(A). When the second member 60 is returned to the first position, the claws 65 of the elastic portions 63 abut on the abutting rib 50 of the first member 40 to restrain the movement of the second member 60. Due to the fact that the second member 60 is returned to the first position, the tip 18 of the hollow needle 17 is accommodated in the cylinder portion 61 of the second member 60.

Next, an operation of discarding the connection device 14 is described with reference to FIGS. 7(A) and 7(C). When a series of operations for obtaining PRP (FIG. 9) are completed, the second member 60 at the first position illustrated in FIG. 7(A) is pulled by a user in the first direction 101 with respect to the first member 40 to be in the state illustrated in FIG. 7(C). The user places a finger on the flange 62, and then pulls the second member 60 in the first direction 101 with respect to the first member 40, for example. When the second member 60 is pulled in the first direction 101, the projection pieces 64 are elastically bent, so that the claws 65 of the elastic portions 63 move beyond the abutting rib 50 of the first member 40. The claws 65 moving beyond the abutting rib 50 are fitted into the concave portion 51 with the elasticity of the bent projection pieces 64. Due to the fact that the claws 65 are fitted into the concave portion 51, the second member 60 is fixed to the first member 40 in the state where the tip 18 of the hollow needle 17 is accommodated. The connection device 14 is discarded in this state.

[Operation of Blood Component Separation Apparatus 10]

An operation of the blood component separation apparatus 10 is described with reference to FIG. 2 and FIG. 9. First, the blood collection needle 15 (FIG. 2) is attached to the syringe barrel 20 of the syringe 11, the plunger 25 (FIG. 2) is attached to the gasket 35, and then blood collection is performed. The blood in the syringe barrel 20 is the whole blood and contains red blood cells, white blood cells, blood platelets, plasma, and the like.

Next, the plunger 25 is removed from the gasket 35 of the syringe 11, and then the syringe barrel 20 of the syringe 11 is attached to a centrifuge (FIG. 9(A)). The removal of the plunger 25 from the gasket 35 can reduce a possibility that the gasket 35 is accidentally moved.

Weak centrifugation is performed by the centrifuge. The weak centrifugation is commonly used in centrifugal separation of blood and is generally defined as "Centrifugal separation of separating the whole blood into red blood cells and other components (white blood cells, blood platelets, plasma)" (Non-patent Literature 1). Specifically, the centrifugal separation in the range where the centrifugal separation conditions are about 500 to 2500 rpm is regarded as the weak centrifugation. The reason for performing the weak centrifugation lies in suppressing concentration of blood platelets near the boundary of the centrifuged division 55 and the centrifuged division 56 which are separated and increasing the concentration of the blood platelets in the obtained PRP. Since the centrifuge is a commonly used one, the detailed explanation is omitted.

In the centrifuge, the syringe barrel 20 is disposed in such a manner that the central axis line is brought into agreement with the radial direction of rotation and the opening 22 side is the rotation center side. Thus, the blood (whole blood) in the syringe barrel 20 is separated into a centrifuged division 56 in the lower side containing red blood cells and the centrifuged division 55 in the upper side containing white blood cells, blood platelets, and plasma.

After the centrifugal separation, the connection device 14 attached to the syringe 12 is inserted into the syringe barrel 20 of the syringe 11 (FIG. 9(B)). The centrifuged division 55 is sucked by the syringe 12 through the hollow needle 17 of the connection device 14. Thus, red blood cells are collected in the syringe 11 and white blood cells, blood platelets, and plasma are collected in the syringe 12. The red blood cells are discarded or are used for another purpose. Then, the connection device 14 is removed from the syringe 12, and then the cap 16 is attached to the syringe barrel 20. The plunger 25 is removed from the syringe 12 (FIG. 9(C)).

Next, the syringe barrel 20 of the syringe 12 is attached to a centrifuge. Strong centrifugation is performed by the centrifuge. The strong centrifugation is commonly used in centrifugal separation of blood and is generally defined as "Centrifugal separation of separating blood platelets, white blood cells, and remaining red blood cells from plasma" (Non-patent Literature 1). In the present invention, the centrifugal separation of concentrating the blood platelets to the bottom portion of the syringe barrel 20 is referred to as the strong centrifugation. Specifically, the centrifugal separation in the range where the centrifugal separation conditions are about 3000 to 4000 rpm is regarded as the strong centrifugation.

In the centrifuge, the syringe barrel 20 is disposed in such a manner that the central axis line is brought into agreement with the radial direction of rotation and the opening 22 side is the rotation center side. Thus, the centrifuged division 55 is separated into PRP in the lower side containing a large number of the blood platelets and the supernatant 57.

After the centrifugal separation, the connection device 14 attached to the syringe 13 is inserted into the syringe barrel 20 of the syringe 12 (FIG. 9(D)). The supernatant 57 is sucked by the syringe 13 through the hollow needle 17 of the connection device 14. Thus, the PRP is obtained in the syringe 12.

The concentration of the blood platelets in the PRP is not always defined clearly. However, when the number of the blood platelets per mL is the concentration of the blood platelets, one in which the concentration of the blood platelets is concentrated to 3 to 7 times as high as the concentration of the blood platelets in the extracted whole blood is regarded as the PRP, for example.

Although this embodiment describes the aspect of performing centrifugal separation twice, the weak centrifugation and the strong centrifugation, the PRP can also be obtained only by one centrifugal separation. Specifically, the strong centrifugation is performed in the syringe barrel 20 of the syringe 11 to separate the whole blood into a centrifuged division in the lower side containing red blood cells, PRP, and a supernatant. The supernatant is sucked by the syringe 12. The plunger 25 is attached to the syringe barrel 20 of the syringe 11, and then the centrifuged division in the lower side containing red blood cells is discharged from the syringe barrel 20. Thus, the PRP is obtained in the syringe 11.

[Effects]

In this embodiment, since the connection device 14 is provided with the hollow needle 17, it is not necessary to pass the hollow needle 17 into the connection device 14. Until when the connection device 14 is inserted into the internal space of the syringe barrel 20 to abut on the gasket 35, the tip 18 of the hollow needle 17 is in the second member 60. After the connection device 14 abuts on the gasket 35 to be pressed into the internal space of the syringe barrel 20, the tip 18 of the hollow needle 17 is in the syringe barrel 20. Therefore, in a series of operations for obtaining the PRP, a user can be prevented from accidentally pricking the user with the hollow needle 17.

Moreover, in this embodiment, the movement of the second member 60 beyond the first position can be restrained by providing the abutting rib 50.

Moreover, in this embodiment, the second member 60 can be fixed to the first member 40 when discarding the connection device, and a possibility that the tip 18 of the hollow needle 17 is accidentally exposed in the discarded connection device 14 can be reduced.

[Modification 1]

Figure 10:
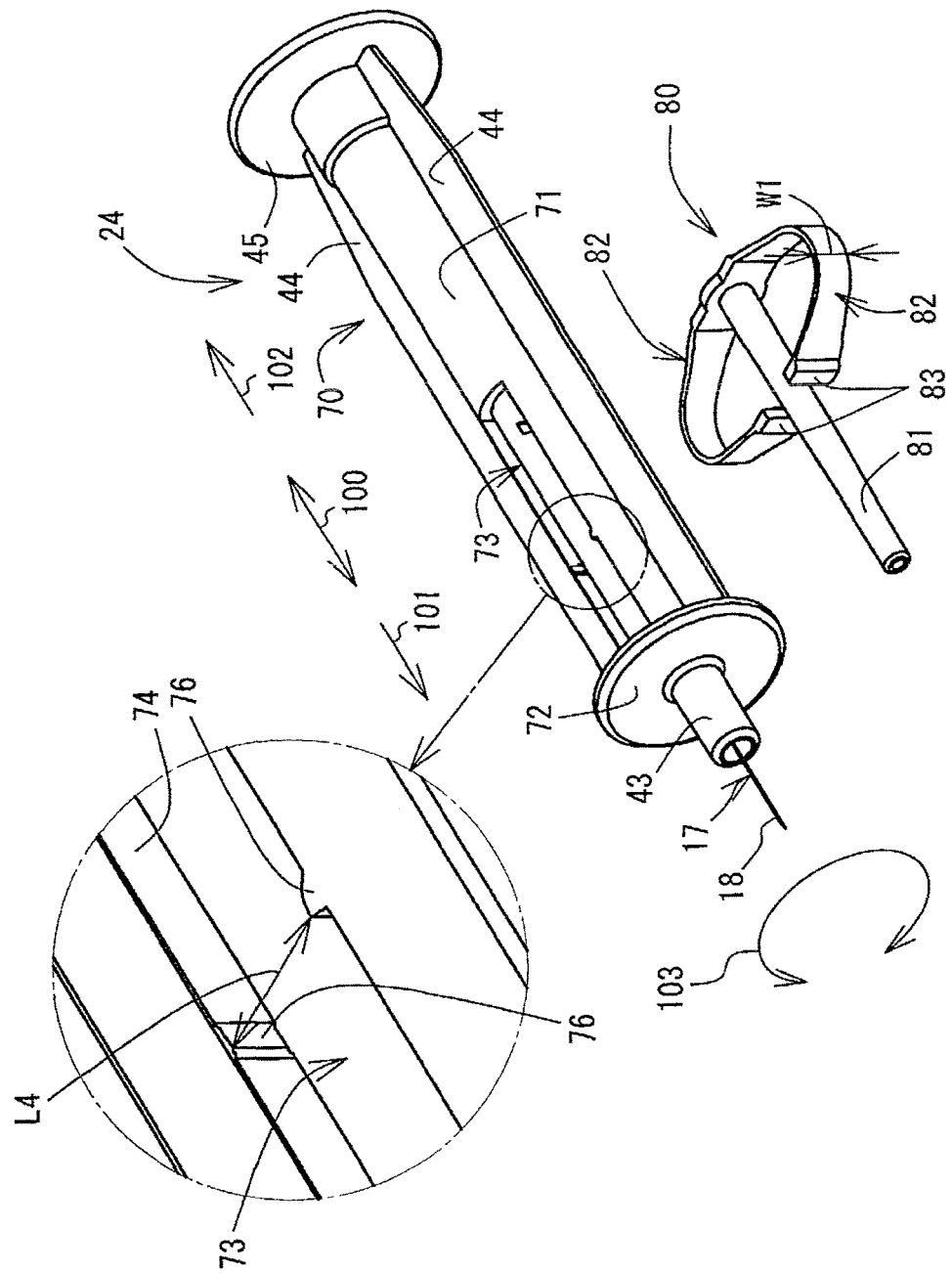
FIG. 10 is an exploded perspective view of a connection device 24 of Modification 1.

This modification describes a connection device 24. In the following description, those having the same configurations as those of the connection device 14 are denoted by the same reference numerals. As illustrated in FIG. 10, the connection device 24 has a first member 70, a second member 80, a hollow needle 17, and a hub 42. The first material 70 is a member which holds the hollow needle 17, and is attached to and detached from syringes 12 and 13. The second member 80 is a member which covers a tip 18 of the hollow needle 17.

[First Member 70]

The first member 70 is a resin molded article of polypropylene or the like having a base 71, reinforcing ribs 44, a first flange 45, and a third flange 72.

The base 71 has a cylindrical shape. The following description is given while defining a direction parallel to the central axis line of the base 71 as an axial direction 100, one direction of the axial direction 100 as a first direction 101, the other direction as a second direction 102, and the circumferential direction of the base 71 as a circumferential direction 103. The axial direction 100 is equivalent to the longitudinal direction. In FIG. 10, the second member 80 is illustrated in the state where the attachment direction of the second member 80 to the first member 70 is rotated by 90° in the circumferential direction 103 so that the configuration of the second member 80 is clearly illustrated.

Figure 11:
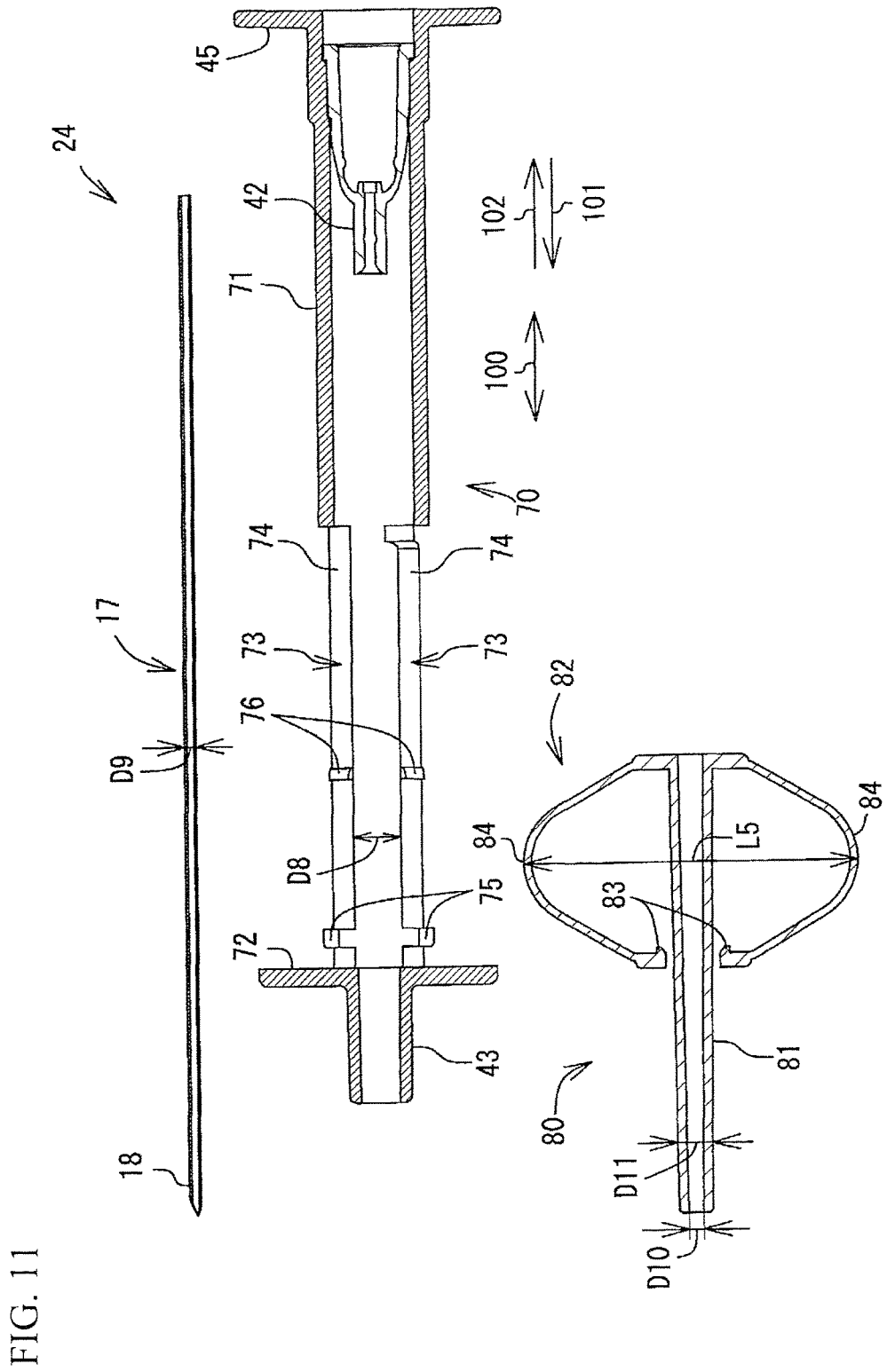
FIG. 11 is an exploded sectional view of the connection device 24 of Modification 1.

As illustrated in FIG. 11, the hub 42 is disposed in the internal space on a side in the second direction 102 of the base 71. The connection device 24 is attached to and detached from the syringe 12 and the syringe 13 through the hub 42. A small diameter portion 43 is provided in an end portion on a side in the first direction 101 of the base 71.

In the internal space (equivalent to the first internal space) of the base 71, a cylinder portion 81 of the second member 80 is disposed. The first member 70 movably supports the second member 80 in the axial direction 100.

Figure 12:
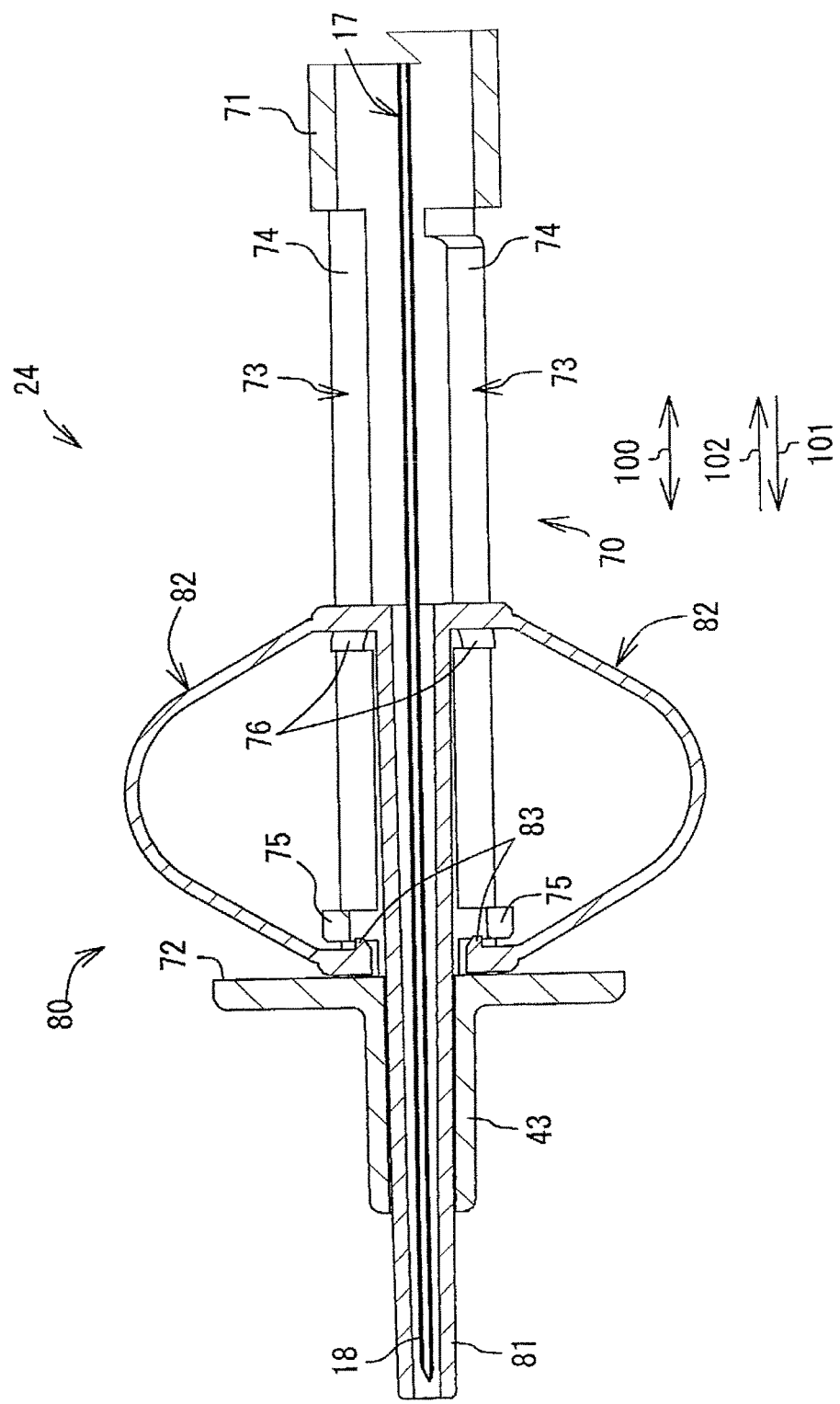
FIG. 12 is a longitudinal sectional view of a connection device 24 of Modification 1.

As illustrated in FIG. 10, the base 71 has two long holes 73 extending in the first direction 101 from the central portion of the base 71 in the axial direction 100. The two long holes 73 are provided penetrating the base 71 in the radial direction at positions facing each other in the radial direction. As illustrated in FIG. 12, elastic pieces 82 of the second member 80 are projected from the internal space of the base 71 toward the outside of the base 71 through the long holes 73.

As illustrated in FIG. 11, from a pair of wall surfaces 74 which face each other in the circumferential direction 103 (FIG. 10) among the wall surfaces of the long holes 73, a pair of projections 75 and a pair of convex portions 76 are projected. The pair of projections 75 are provided on an end portion on a side in the first direction 101 of the wall surfaces 74 and face each other in the circumferential direction 103. The projections 75 are provided apart from a third flange 72 described later on a side in the second direction 102 of the flange 72. As illustrated in FIG. 12, claws 83 provided at the tip of the elastic pieces 82 of the second member 80 are press-fitted between the third flange 72 and the projections 75. The claws 83 are caught in the projections 75 and latched by the projections 75.

As illustrated in FIG. 10, a pair of convex portions 76 are provided at almost the central portion of the wall surfaces 74 in the axial direction 100 and face each other in the circumferential direction 103. A distance L4 between the tips of projections of the pair of convex portion 76 is made slightly shorter than a width W1 of the elastic pieces 82. Specifically, the distance L4 is made shorter than the width W1 in such a manner that the elastic pieces 82 can pass through between the pair of convex portions 76 by elastic deformation of the elastic pieces 82 and elastic deformation of the convex portions 76. The convex portions 76 abut on the elastic pieces 82 to fix the second member 80 before the connection device 24 is discarded as described later. The surface on a side in the second direction 102 of the pair of convex portions 76 is formed into a curved surface in such a manner that the elastic pieces 82 can pass. Moreover, sides in the first direction 101 of the tips of projections of the pair of convex portions 76 are edged in such a manner that the second member 80 does not return to the first position. The pair of convex portions 76 are equivalent to the engagement portion and the lock mechanism.

The third flange 72 has the same configuration as that of the second flange 46 except that the insertion holes 47 are not provided.

Two reinforcing ribs 44 extend in the axial direction 100 from the first flange 45 to the third flange 72. The reinforcing ribs 44 are shifted by only 90° in the circumferential direction 103 with respect to the long holes 73 in such a manner as not to overlap with the long holes 73 of the base 71.

[Second Member 80]

The second member 80 has a cylinder portion 81 and a pair of elastic pieces 82 extending from the cylinder portion 81. The second member 80 is a resin molded article molded with polypropylene or the like. Therefore, the elastic pieces 82 of the second member 80 can be elastically deformed.

As illustrated in FIG. 11, the cylinder portion 81 has a cylindrical shape in which an outer diameter D11 is smaller than an internal diameter D8 of the base 71. The cylinder portion 81 is inserted into the base 71 from an opening on a side in the first direction 101 of the base 71. The second member 80 is guided in the axial direction 100 in the cylinder portion 81. The second member 80 is moved back and forth in the axial direction 100 relative to the first member 70 between a first position illustrated in FIG. 13(A) and a second position illustrated in FIG. 13(B). The internal space of the cylinder portion 81 is equivalent to the second internal space.

As illustrated in FIG. 12, the elastic pieces 82 are extended from an end portion on a side in the second direction 102 of the cylinder portion 81. The elastic pieces 82 are curved in a chevron shape and are projected from the internal space of the base 71 toward the outside of the base 71 through the long holes 73. The tips of the elastic pieces 82 are inserted between the third flange 72 and the projections 75. The elastic pieces 82 have claws 83 caught in the projections 75 at the tips. The tips of the elastic pieces 82 are latched by the first member 70 due to the claws 83.

Figure 14:
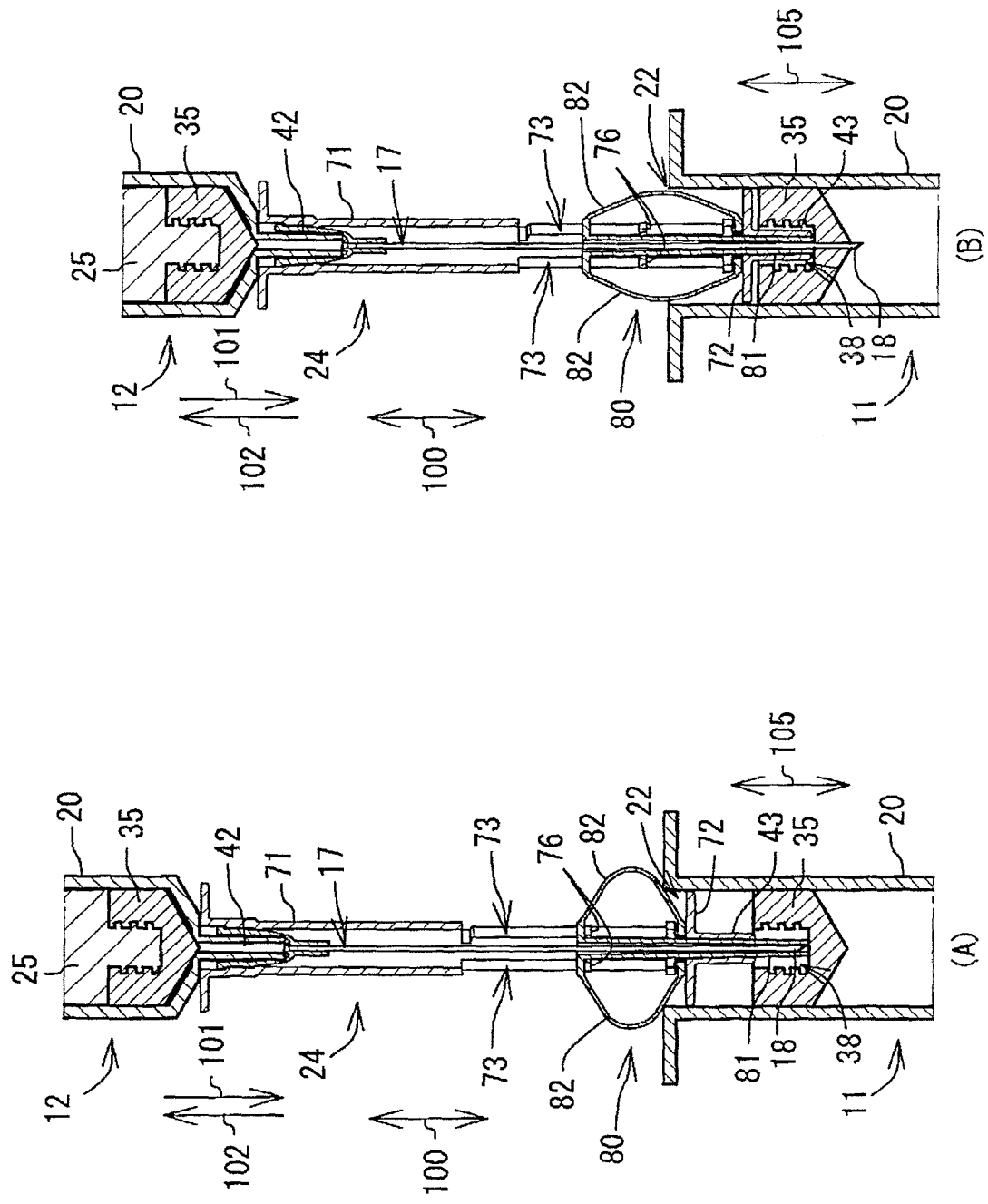
FIG. 14 includes views explaining an operation of the connection device 24 of Modification 1 when inserted into the syringe barrel 20.

As illustrated in FIG. 11, a distance L5 between top portions 84 of the pair of chevron-shaped elastic pieces 82 in the radial direction of the base 71 is made longer than the internal diameter D2 (FIG. 3) of the syringe barrel 20. As illustrated in FIG. 14, when the connection device 24 is inserted into the syringe barrel 20, the elastic pieces 82 abut on the edge of an opening 22 of the syringe barrel 20.

[Hollow Needle 17]

As illustrated in FIG. 11, an outer diameter D9 of the hollow needle 17 is made smaller than an internal diameter D10 of the cylinder portion 81. As illustrated in FIG. 12, the hollow needle 17 is disposed in the cylinder portion 81 and the base 71 and is connected to the hub 42 (FIG. 11) at the base end. The tip of the hollow needle 17 is projected in the first direction 101 by only a projection amount L3 (FIG. 7) from the small diameter portion 43 of the first member 70. Thus, the hollow needle 17 can penetrate a gasket 35 (FIG. 14(B)). When the second member 80 is positioned at a first position illustrated in FIG. 13(A), the tip 18 of the hollow needle 17 is accommodated in the second member 80. When the second member 80 is positioned at a second position illustrated in FIG. 13(B), the tip 18 of the hollow needle 17 is exposed.

[Operation of Connection Device 24]

Figure 13:
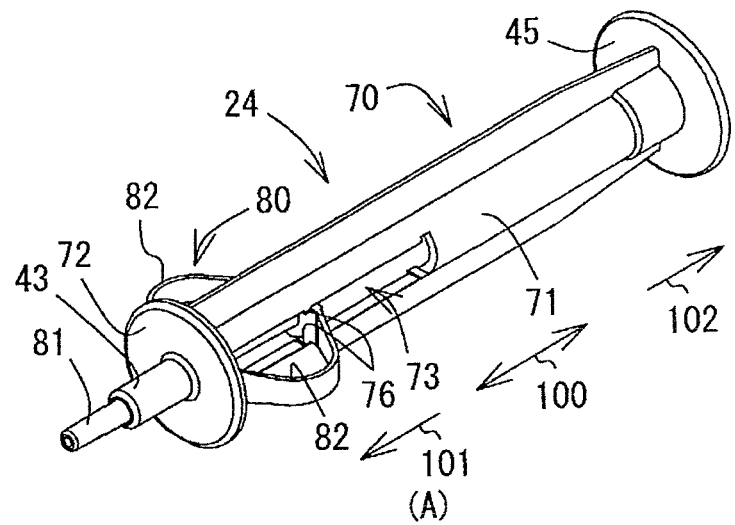
FIG. 13 includes views explaining an operation of the connection device 24 of Modification 1.
Figure 13:
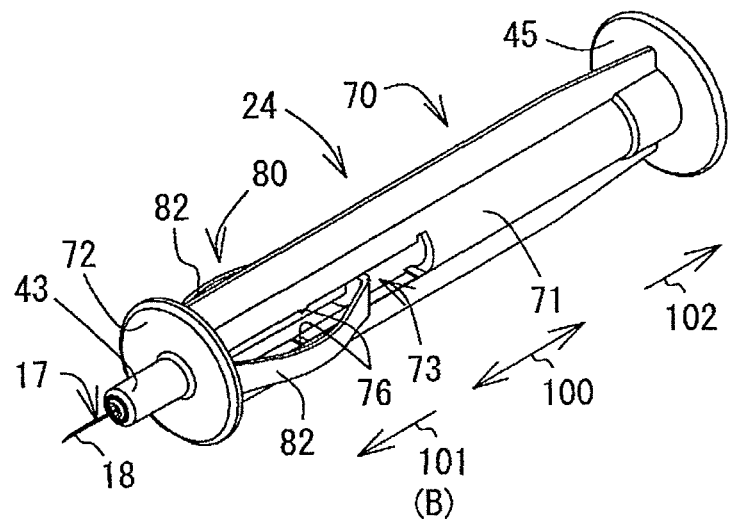
Figure 13:
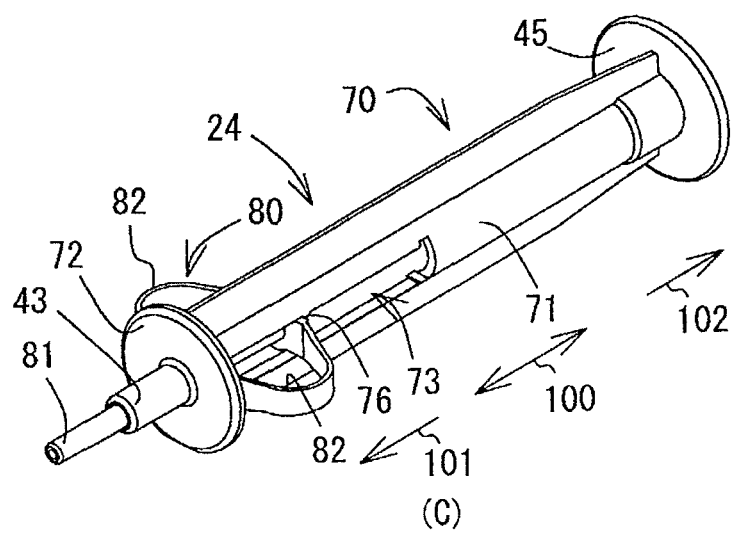

An operation when the connection device 24 is attached to the syringe 12 and inserted into the syringe barrel 20 of the syringe 11 is described with reference to FIG. 13 and FIG. 14.

The connection device 24 is attached to the syringe barrel 20 of the syringe 12 through the hub 42. A user holds the first member 90 in the hand to attach the connection device 34 to the syringe 12. The connection device 24 may be attached to the syringe 12 in manufacturing.

When the connection device 24 is not inserted into the syringe barrel 20 of the syringe 11, the second member 80 is positioned at the first position illustrated in FIG. 13(A). The second member 80 at the first position accommodates the tip 18 of the hollow needle 17.

As illustrated in FIG. 14(A), when the connection device 24 is inserted into the syringe barrel 20 from the side of the tip 18 of the hollow needle 17, the elastic pieces 82 abut on the edge of the opening 22 of the syringe barrel 20 of the syringe 11. The cylinder portion 81 abuts on the bottom surface of a screw hole 38 of the gasket 35 of the syringe 11. When the connection device 24 is further pressed into the syringe barrel 20, the elastic pieces 82 and the cylinder portion 81 are pressed in the second direction 102 by the syringe barrel 20 and the gasket 35 to be moved to the second position illustrated in FIG. 14(B). Thus, the elastic pieces 82 are elastically deformed at the tip latched by the first member 70 as the base point to be elastically deformed from the chevron shape illustrated in FIG. 14(A) to a gentle chevron shape close to a linear shape illustrated in FIG. 14(B). The elastically deformed elastic pieces 82 elastically energize the cylinder portion 81 in the first direction 101 with respect to the first member 70.

The cylinder portion 81 is moved from the first position to the second position by being pressed in the second direction 102 by the gasket 35 or by the elastic deformation of the elastic pieces 82. Thus, the tip 18 of the hollow needle 17 is exposed. As illustrated in FIG. 14(B), the tip 18 of the exposed hollow needle 17 is stuck into the bottom surface of the screw hole 38 of the gasket 35, and penetrates the gasket 35.

As illustrated in FIG. 14(B), the elastic pieces 82 are positioned inside the inner circumferential surface of the syringe barrel 20 at the second position where the hollow needle 17 penetrates the gasket 35, and are not further elastically deformed. Moreover, at the second position, a cylinder 81 is positioned inside the small diameter portion 43, and is not further pressed by the gasket 35. Therefore, the second member 80 is not moved beyond the second position.

When the connection device 24 is removed from the syringe barrel 20, the second member 80 is moved to the first position illustrated in FIG. 13(A) from the second position illustrated in FIG. 13(B) with the elasticity of the elastic pieces 82, and covers the tip 18 of the hollow needle 17. When the second member 80 is moved to the first position, the elastic pieces 82 abut on the pair of convex portions 76. Thus, the movement of the second member 80 beyond the first position is restrained.

Next, an operation of the connection device 24 when the connection device 24 is discarded is described with reference to FIG. 13. After a series of operations for obtaining PRP (FIG. 9) are completed, the second member 80 at the first position illustrated in FIG. 13(A) is moved in the first direction 101 with respect to the first member 70 by a user. The user moves the second member 80 with respect to the first member 70 by holding the cylinder portion 81, and then pulling the same in the first direction 101 or pressing the elastic pieces 82 in the first direction 101, for example. When the second member 80 is moved, the elastic pieces 82 pass through between the pair of convex portions 76 by the elastic deformation of the elastic pieces 82 or the elastic deformation of the convex portions 76. Due to the fact that the elastic pieces 82 pass through between the pair of convex portions 76, the second member 80 is fixed to the first member 70 (FIG. 13(C)). The connection device 24 is discarded in this state.

[Effects]

In this modification, since the hollow needle 17 is formed in the connection device 24, it is not necessary to pass the hollow needle 17 into the connection device 24. Moreover, when the connection device 24 is not inserted into the internal space of the syringe barrel 20, the tip 18 of the hollow needle 17 is in the second member 80 and when the connection device 24 is inserted into the syringe barrel 20, the tip 18 of the hollow needle 17 is in the syringe barrel 20. Therefore, in a series of operations for obtaining PRP, a user can be prevented from accidentally pricking the user with the hollow needle 17.

Moreover, in this modification, since the second member 80 can be fixed to the first member 70 when discarding the connection device 24, a possibility that the tip 18 of the hollow needle 17 is accidentally exposed in the discarded connection device 24 can be reduced.

This modification describes the example in which the elastic pieces 82 are provided in such a manner as to abut on the edge of the opening 22 of the syringe barrel 20 when the tip of the cylinder portion 81 abuts on the bottom surface of the screw hole 38 of the gasket 35. However, the elastic pieces 82 may be provided in such a manner as to abut on the edge of the opening 22 of the syringe barrel 20 before the cylinder portion 81 abuts on the bottom surface of the screw hole 38.

[Modification 2]

Figure 15:
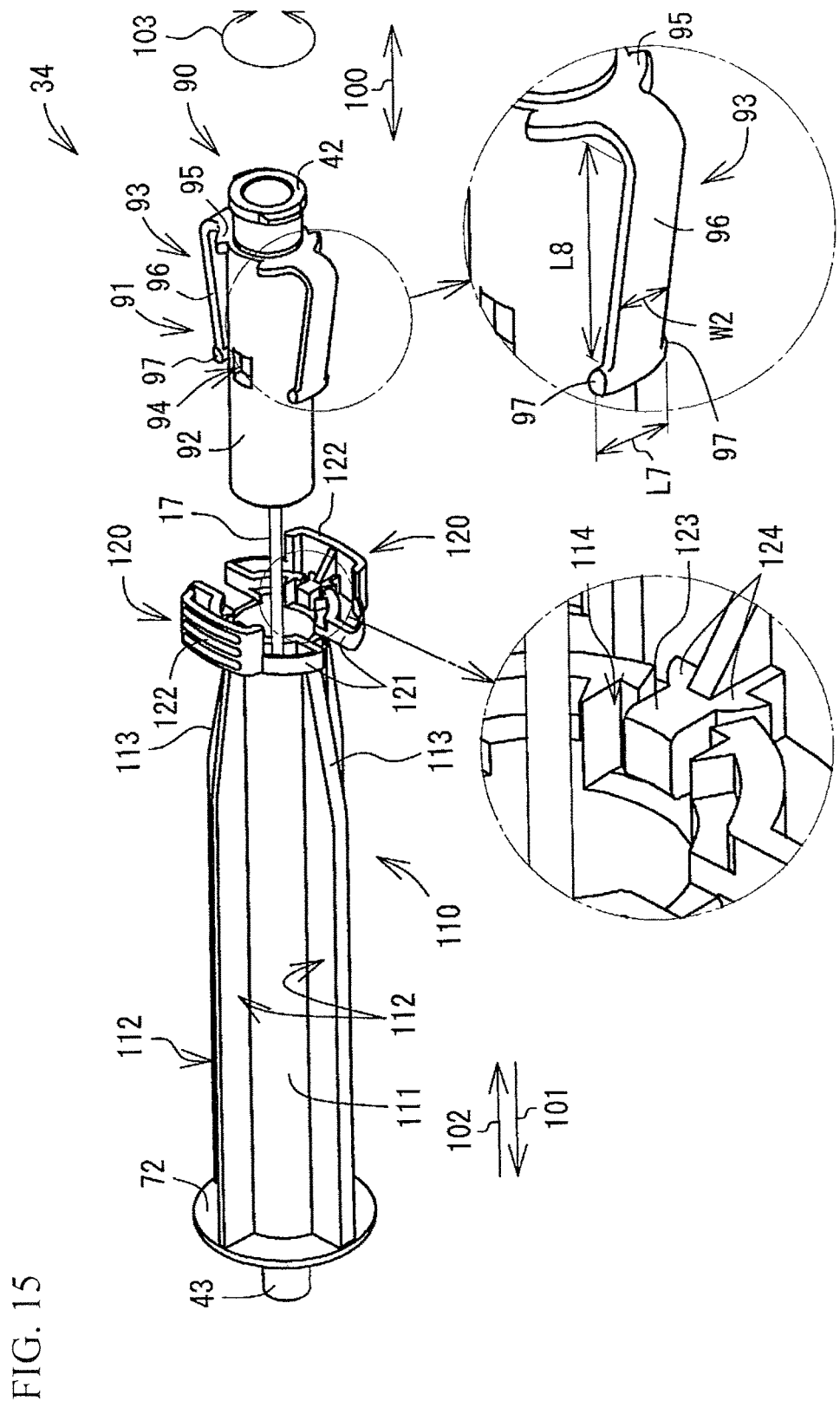
FIG. 15 is an exploded perspective view of a connection device 34 of Modification 2.

This modification describes a connection device 34 illustrated in FIG. 15. In the following description, those having the same configurations as those of the connection device 14 and the connection device 24 are denoted by the same reference numerals.

The connection device 34 has a first member 90, a second member 110, a hollow needle 17, and a hub 42. The first member 90 is a member which holds the hollow needle 17 and the hub 42. The second member 110 is a member which covers a tip 18 of the hollow needle 17.

[First Member 90]

The first member 90 is a resin molded article of polypropylene or the like having a cylinder portion 92 having a cylindrical shape and elastic portions 93 extended from the cylinder portion 92. Therefore, the elastic portions 93 can be elastically deformed. The following description is given while defining a direction parallel to the central axis line of the cylinder portion 92 as an axial direction 100, one direction of the axial direction 100 as a first direction 101, the other direction as a second direction 102, and the circumferential direction of the cylinder portion 92 as a circumferential direction 103. The axial direction 100 is equivalent to the longitudinal direction.

The hub 42 is inserted into the internal space (equivalent to the first internal space) of the cylinder portion 92 from an opening on a side in the second direction 102 of the cylinder portion 92 and is attached to the first member 90.

The first member 90 is moved relative to the second member 110 in the axial direction 100 in the internal space (equivalent to the second internal space) of a base 111 of the second member 110 as described later.

Figure 17:
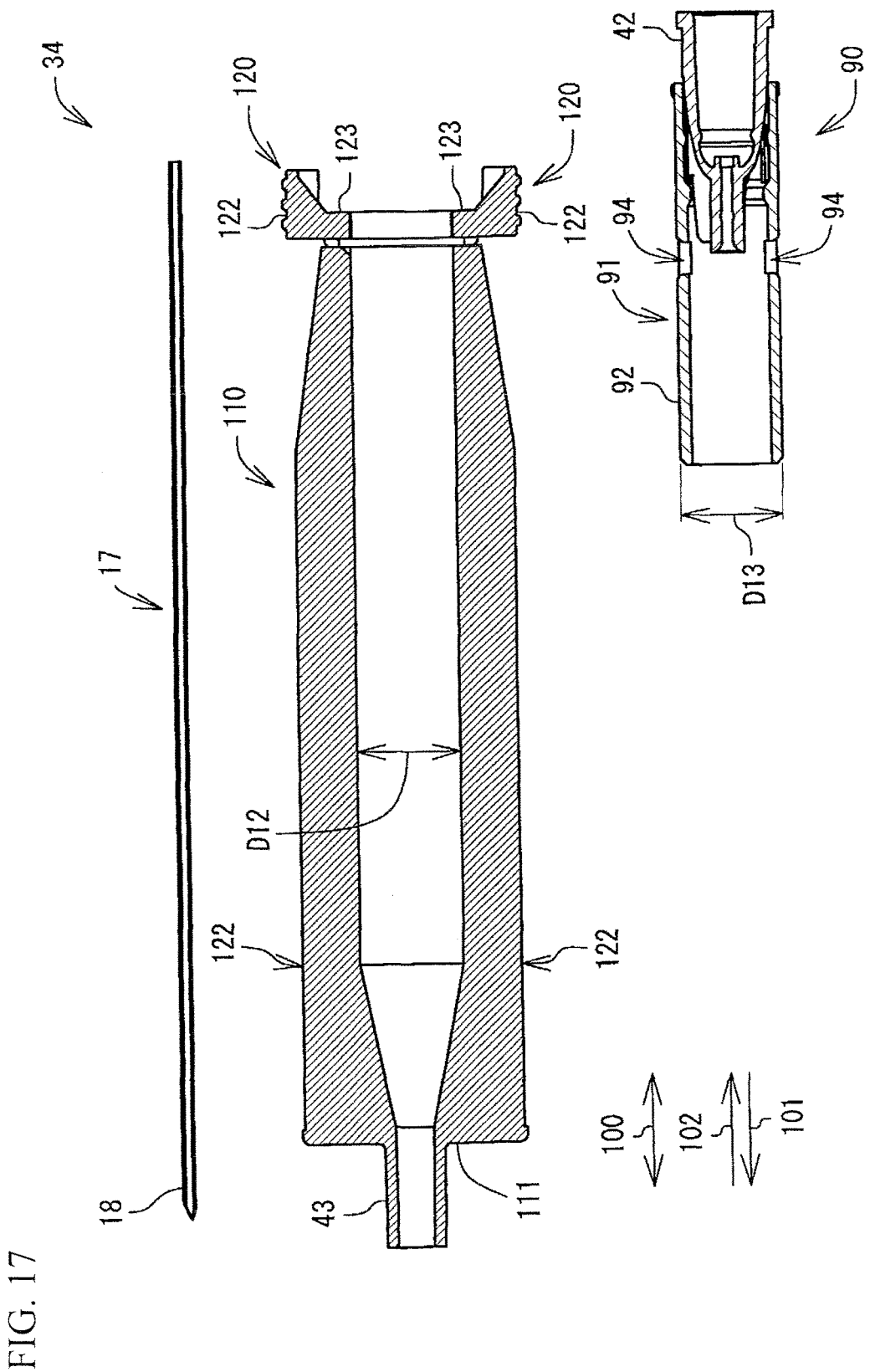
FIG. 17 is an exploded sectional view of a connection device 34 of Modification 2.

As illustrated in FIG. 17, the cylinder portion 92 has a pair of through-holes 94. The pair of through-holes 94 penetrate the cylinder portion 92 at positions facing each other in the radial direction of the cylinder portion 92. The through-holes 94 are formed at almost the central portion in the axial direction 100 of the cylinder portion 92. When the connection device 34 is discarded, engagement convex portions 123 of the second member 110 are fitted into the through-holes 94. Thus, the first member 90 is fixed to the second member 110. The through-holes 94 are equivalent to the engagement concave portion.

As illustrated in FIG. 15, the elastic portion 93 has a flange 95, a projection piece 96, and a pair of bosses 97. The flange 95 is projected in the radial direction from the end on a side in the second direction 102 of the outer circumferential surface of the cylinder portion 92. As illustrated in FIG. 18(B), the flange 95 abuts on the base 111 of the second member 110, and restrains relative movement in the axial direction 100 of the first member 90 and the second member 110.

As illustrated in FIG. 15, the projection pieces 96 are projected in the first direction 101 from the flange 95. In the relative movement of the first member 90 and the second member 110, the projection pieces 96 slide on inclines 113 of the second member 110 to be elastically bent. The bent projection pieces 96 elastically energize the second member 110 in the first direction 101 with respect to the first member 90.

The pair of bosses 97 are projected in the circumferential direction 103 from both side surfaces in the circumferential direction 103 at the tips of the projection pieces 96. As illustrated in FIG. 18(A), the bosses 97 abut on elastic pieces 121 of the second member 110, and restrains relative movement in the axial direction 100 of the first member 90 and the second member 110.

The first member 90 is restrained from moving relative to the second member 110 by the abutting of the bosses 97 on the elastic pieces 121 and the abutting of the flange 95 on the base 111. Therefore, the moving range of the first member 90 to the second member 110 in the axial direction 100 is within the range of a length L8 (FIG. 15) of the projection pieces 96 in the axial direction 100. The length L8 of the projection pieces 96 is made longer than a thickness T (FIG. 3) of a gasket 35 in such a manner that the tip 18 of the hollow needle 17 can penetrate the gasket 35 (FIG. 3).

[Hollow Needle 17]

Figure 16:
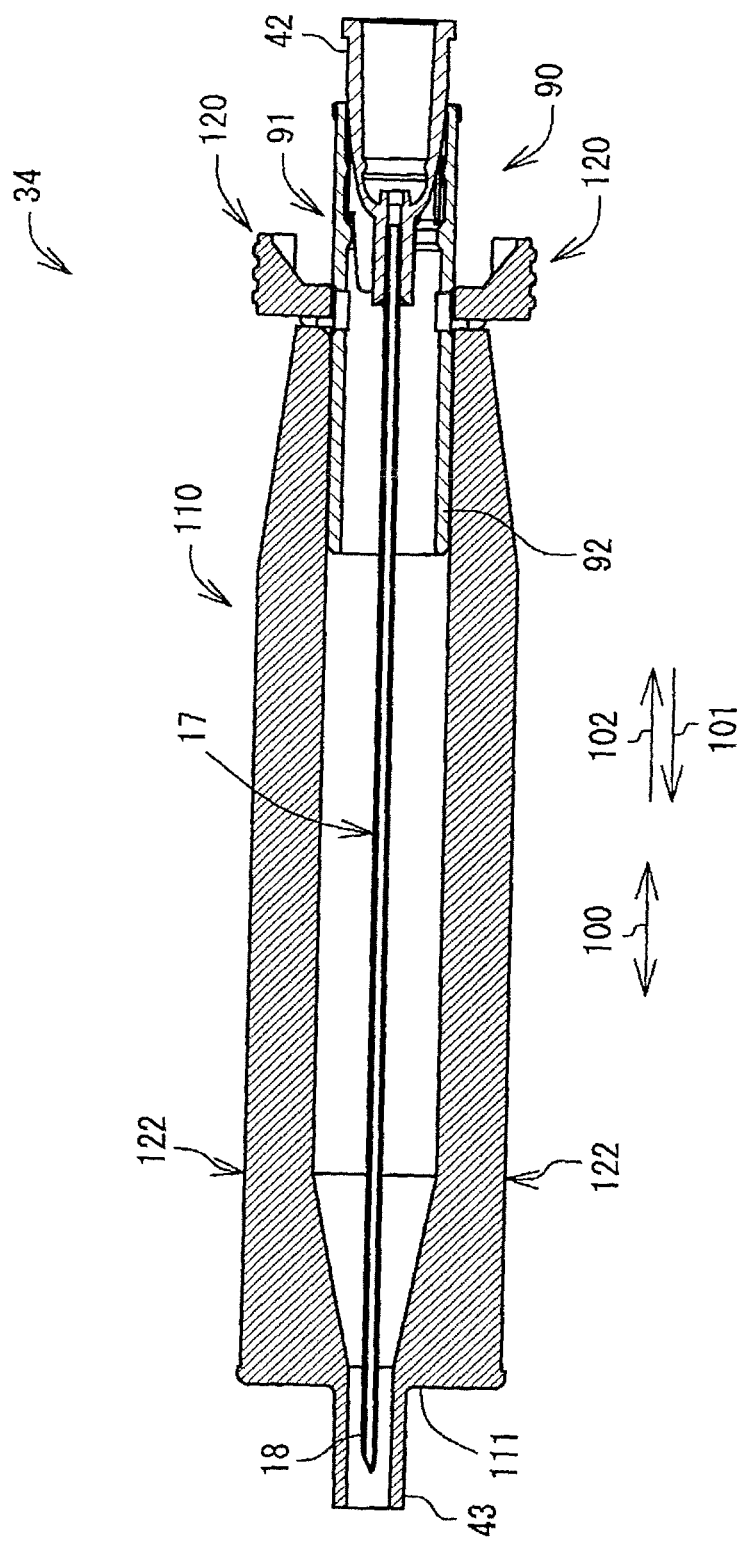
FIG. 16 is a longitudinal sectional view of the connection device 34 of Modification 2.

As illustrated in FIG. 16, the hollow needle 17 is connected to the hub 42 at the base end and is projected in the first direction 101 from the first member 90.

[Second Member 110]

As illustrated in FIG. 15, the second member 110 is a resin molded article of polypropylene or the like having a base 111, four reinforcing ribs 112, a third flange 72, and lock mechanisms 120.

The base 111 has a cylindrical shape extending in the axial direction 100. As illustrated in FIG. 17, an internal diameter D12 of the base 111 is made slightly larger than an outer diameter D13 of the cylinder portion 92 of the first member 90. The cylinder portion 92 is inserted into the base 111 from an opening on a side in the second direction 102 of the base 111. The base 311 is guided in the axial direction 100 by the cylinder portion 92. The second member 110 is moved back and forth relative to the first member 90 in the axial direction 100 between a first position illustrated in FIG. 18(A) and a second position illustrated in FIG. 18(B).

A small diameter portion 43 is provided on an end portion on a side in the first direction 101 of the base 111. As illustrated in FIG. 16, the base 111 is set to a length according to the length of the hollow needle 17 in the axial direction 100 in such a manner that the small diameter portion 43 covers the tip 18 of the hollow needle 17 at the first position.

Figure 18:
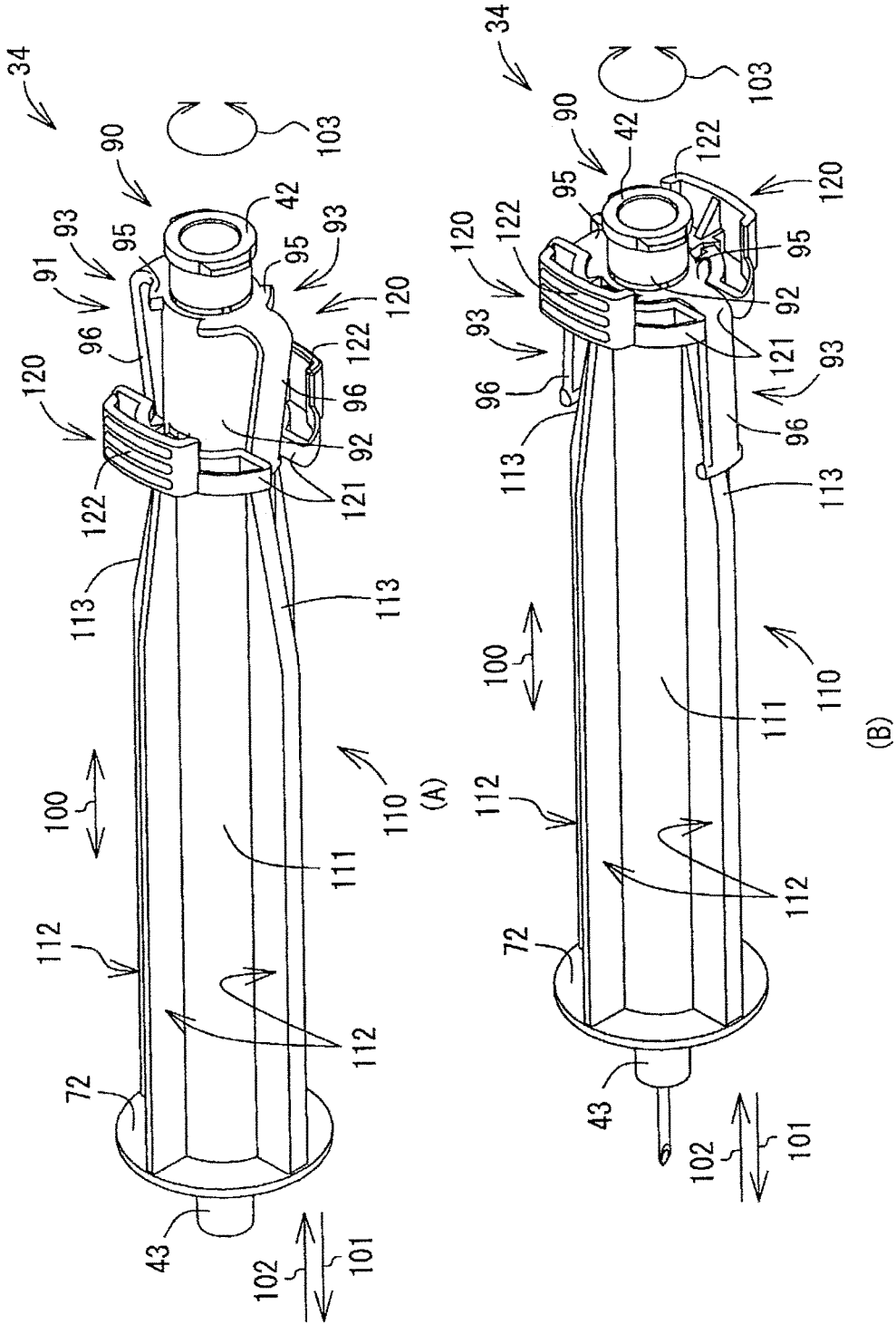
FIG. 18 includes views explaining an operation of the connection device 34 of Modification 2.

The reinforcing ribs 112 are projected in the radial direction from the outer circumferential surface of the base 111 and extend in the axial direction 100. The four reinforcing ribs 112 are disposed at an interval of 90° in the circumferential direction 103. The tip surfaces of projections of the reinforcing ribs 112 on a side in the second direction 102 constitute inclines 113 approaching the outer circumferential surface of the base 11 toward the second direction 102. As illustrated in FIG. 18, when the first member 90 and the second member 110 are relatively moved in the axial direction 100, the projection pieces 96 of the first member 90 slide on the inclines 113.

A pair of lock mechanisms 120 are provided on the end on a side in the second direction 102 of the base 131 facing each other in the radial direction of the base 111. The lock mechanism 120 has the elastic pieces 121, a holding portion 122 provided to the elastic pieces 121, and an engagement convex portion 123 projected from the holding portion 122.

The elastic piece 121 is constituted in an approximately U shape, which is elastically deformed, and one end thereof is joined to the base 111 and the other end is joined to the holding portion 122. Thus, the elastic piece 121 elastically energizes the holding portion 122 to the outside in the radial direction of the base 111. The elastic piece 121 is equivalent to the energizing portion. In more detail, a pair of the elastic pieces 121 are provided on both sides of the holding portion 122 in the circumferential direction of the second member 110. The holding portion 122 is elastically supported by both the pair of elastic pieces 121.

Figure 19:
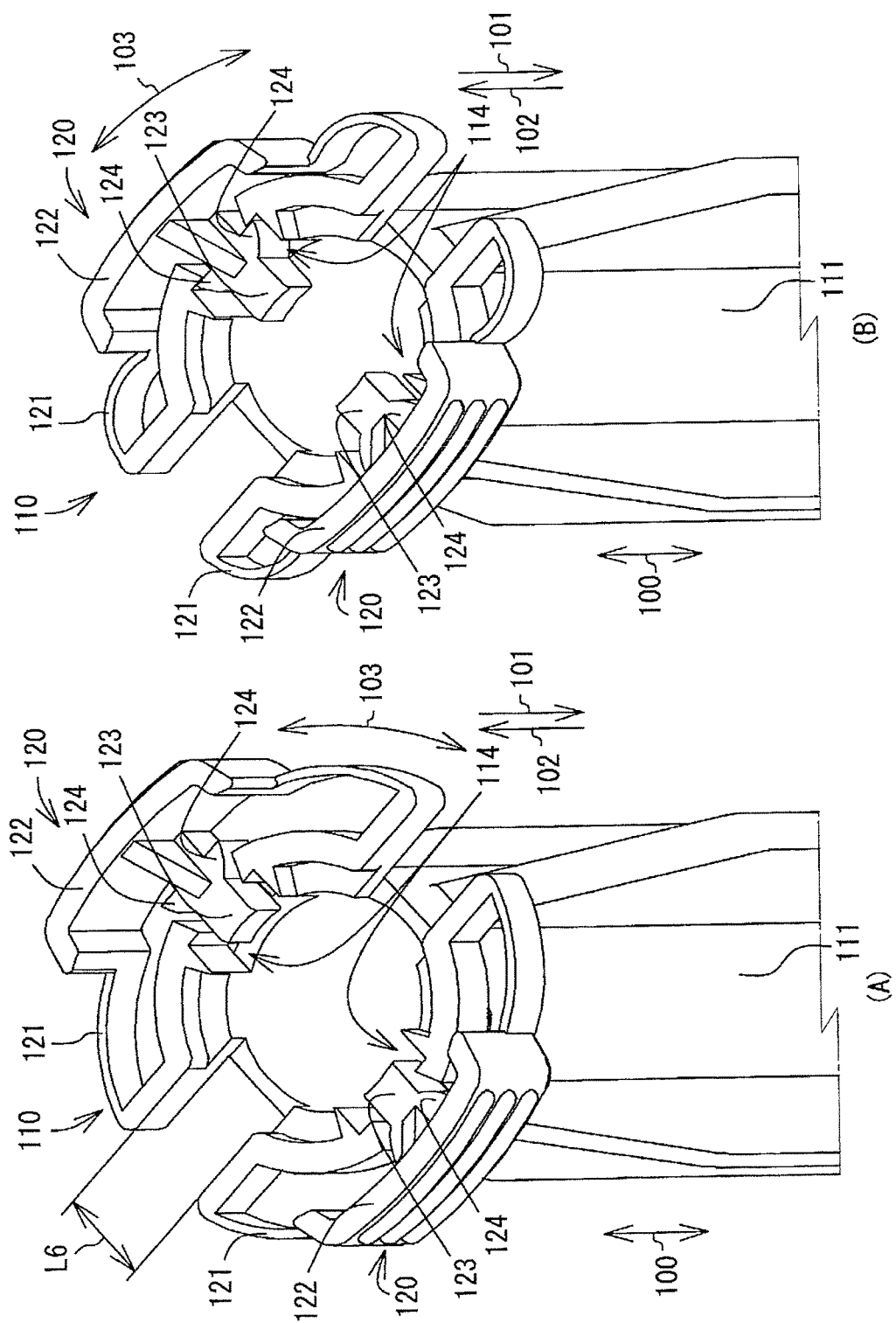
FIG. 19 includes views explaining an operation of lock mechanisms 120 of Modification 2.

The elastic pieces 121 of one lock mechanism 120 and the elastic pieces 121 of the other lock mechanism 120 are separated only by a distance L6 (FIG. 19(A)) in the radial direction of the base 111. The distance L6 is made longer than a width W2 (FIG. 15) of the projection pieces 96 of the first member 90. As illustrated in FIG. 18, the projection pieces 96 are extended to the inclines 113 through between the pair of elastic pieces 121, and abut on the inclines 113 at the tip. The distance L6 is made shorter than a distance L7 (FIG. 15) between the tips of projections of the pair of bosses 97 of the first member 90. As illustrated in FIG.

18(A), when the first member 90 and the second member 110 are relatively moved in the axial direction 100, the bosses 97 abut on the elastic pieces 121, so that the relative movement of the first member 90 and the second member 110 is restrained.

As illustrated in FIG. 15, the holding portion 122 is provided in the middle of the pair of elastic pieces 121. The holding portion 122 has a plate shape along the outer circumferential surface of the base 111. The holding portion 122 supports the engagement convex portion 123 facing the through-hole 94 of the first member 90 in the state where the second member 110 is attached to the first member 90. The pair of holding portions 122 of the pair of lock mechanisms 120 face each other in the radial direction of the base 111. When the pair of holding portions 122 are held by a user, the elastic pieces 121 are elastically deformed, so that the holding portions 122 abut on the outer circumferential surface of the base 111 (FIG. 19(B)).

The engagement convex portions 123 are projected from the holding portions 122 toward the central portion of the base 111. A pair of notches 114 which are notched from the end surface on a side in the second direction 102 are provided in the base 111, and the tips of the engagement convex portions 123 are located in the notches 114. The notches 114 are located between end portions of the sides joined to the base 11 of the pair of elastic pieces 121 which constitute the lock mechanisms 120. More specifically, the edge of the notch 114 serves as an end portion of the side joined to the base 111 of the elastic piece 121. When the holding portions 122 are pressed by a user and the holding portions 122 abut on the outer circumferential surface of the base 111, the tips of the engagement convex portions 123 are projected to the inside of the inner circumferential surface of the base 111 (FIG. 19(B)) to be fitted into the through-holes 94 of the first member 90 at the first position (FIG. 20(B)).

As illustrated in FIG. 15, a pair of projections 124 in a triangular shape as viewed in plane are projected in the circumferential direction 103 from both the side surfaces of the engagement convex portions 123 in the circumferential direction 103. In more detail, the projections 124 are projected from the engagement convex portion 123 to each of the pair of elastic pieces 121. When the holding portions 122 are held by a user and the holding portions 122 abut on the outer circumferential surface of the base 111 (FIG. 19(B)), the pair of projections 124 are caught in the edges of the notches 114 of the base 111 (i.e., engage with each of the pair of elastic pieces 121), and then latched by the base 111. Thus, the first member 90 is fixed to the second member 110. The projections 124 are equivalent to the lock portion.

[Operation of Connection Device 34]

Figure 21:
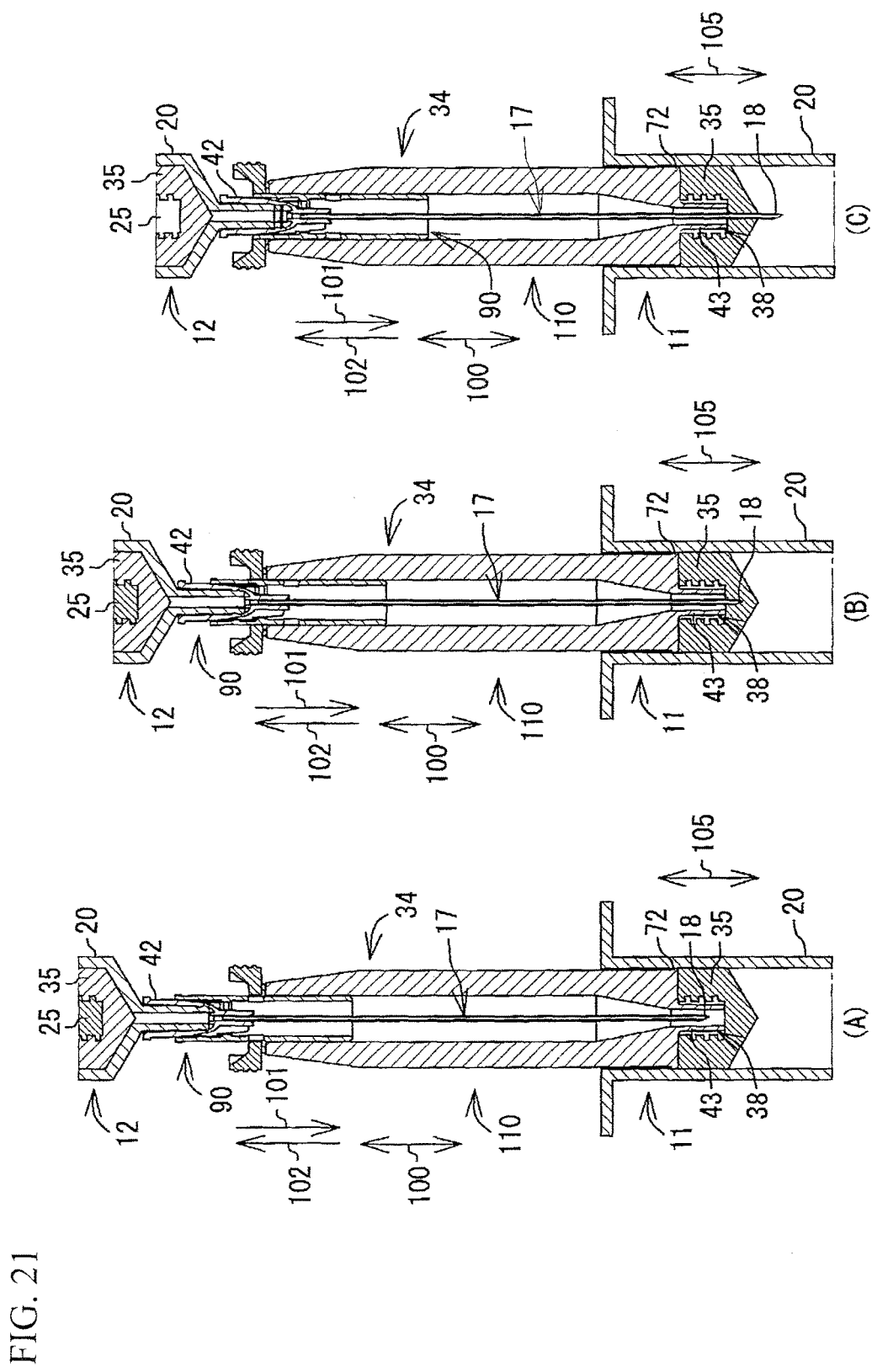
FIG. 21 includes views explaining a procedure of using the connection device 24 of Modification 2.

An operation when the connection device 34 is attached to the syringe 12 and inserted into the syringe barrel 20 of the syringe 11 is described with reference to FIG. 18 and FIG. 21.

A user holds the first member 90 in the hand to attach the connection device 34 to the syringe 12. In manufacturing, the connection device 34 may be attached to the syringe 12.

As illustrated in FIG. 18(A), before the connection device 34 is inserted into the syringe barrel 20 of the syringe 11, the tip 18 of the hollow needle 17 is covered with the second member 110.

As illustrated in FIG. 21(A), the connection device 34 attached to the syringe 12 is inserted into the syringe barrel 20 of the syringe 11 from the side of the small diameter portion 43. Thus, the small diameter portion 43 abuts on the bottom surface of the screw hole 38 of the gasket 35 of the syringe 11. In this state, when the first member 90 is pressed by a user through the syringe 12, the second member 110 is moved relative to the first member 90 in the axial direction 100 as illustrated in FIG. 21(B). Thus, the tip 18 of the hollow needle 17 is projected from the small diameter portion 43 to be stuck into the gasket 35. When the first member 90 is further pressed in a downward direction, the second member 110 reaches the second position, so that the hollow needle 17 penetrates the gasket 35.

As illustrated in FIG. 18, when the second member 110 is moved to the second position from the first position, the projection pieces 96 slide on the inclines 113 to be elastically bent. The bent projection pieces 96 elastically energize the second member 110 in the second direction 102 with respect to the first member 90.

When the connection device 34 is removed from the syringe barrel 20 of the syringe 11, the second member 110 is moved in the second direction 102 with respect to the first member 90 with the elasticity of the bent projection pieces 96 to be returned to the first position. Thus, the tip 18 of the hollow needle 17 is covered with the small diameter portion 43.

Figure 20:
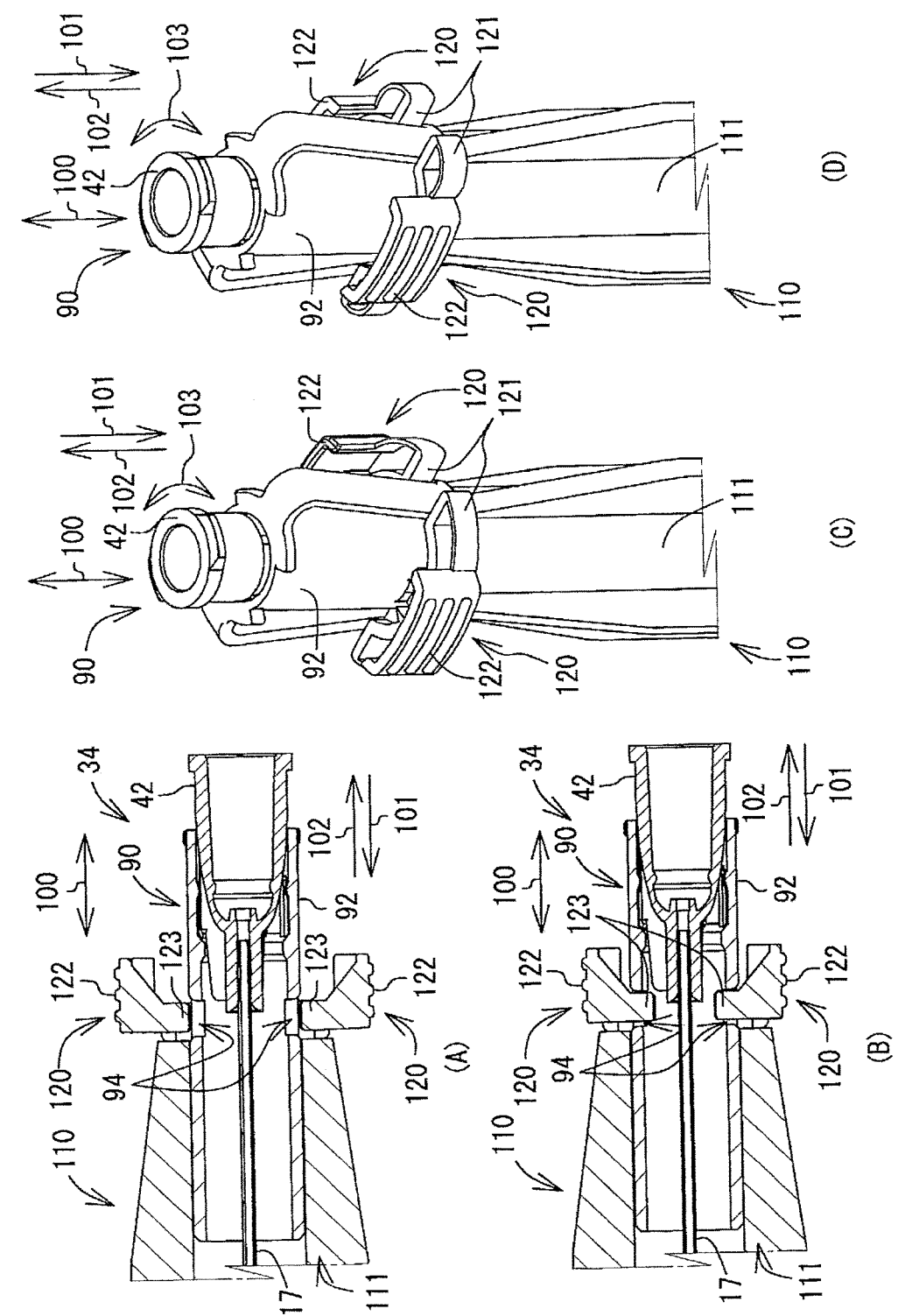
FIG. 20 includes views explaining an operation when a first member 90 is fixed to a second member 110 in Modification 2.

Next, an operation for discarding the connection device 34 is described with reference to FIG. 20. After a series of operations for obtaining PRP (FIG. 9) are completed, the pair of holding portions 122 are held by a user. Thus, the lock mechanisms 120 are moved to a position illustrated in FIGS. 20(B) and 20(D) from a position illustrated in FIGS. 20(A) and 20(C) by the elastic deformation of the elastic pieces 121. Thus, the engagement convex portions 123 of the lock mechanisms 120 are fitted into the through-holes 94 of the first member 90, and the projections 124 are caught in the edges of the notches 114 (FIG. 19(A)). More specifically, the pair of projections 124 and end portions of the sides joined to the base 111 of the pair of elastic pieces 121 are engaged with each other. Thus, the first member 90 is fixed to the second member 110 in the state where the second member 110 accommodates the tip 18 of the hollow needle 17. The connection device 34 is discarded in this state.

[Effects]

In this modification, since the hollow needle 17 is provided in the connection device 34, it is not necessary to pass the hollow needle 17 into the connection device 34. Moreover, the tip 18 of the hollow needle 17 is in the second member 60 and abuts on the gasket 35 until the connection device 34 is inserted into the internal space of the syringe barrel 20 and abuts on the gasket 35 and the tip 18 of the hollow needle 17 is in the syringe barrel 20 after the connection device 34 abuts on the gasket 35, and is further pressed into the internal space of the syringe barrel 20. Therefore, in a series of operations for obtaining PRP, a user can be prevented from accidentally pricking the user with the hollow needle 17.

Moreover, in this modification, since the first member 90 can be fixed to the second member 110 by the lock mechanisms 120 when discarding the connection device 34, a possibility that the tip 18 of the hollow needle 17 is accidentally exposed in the discarded connection device 34 is reduced.

[Modification 3]

Figure 22:
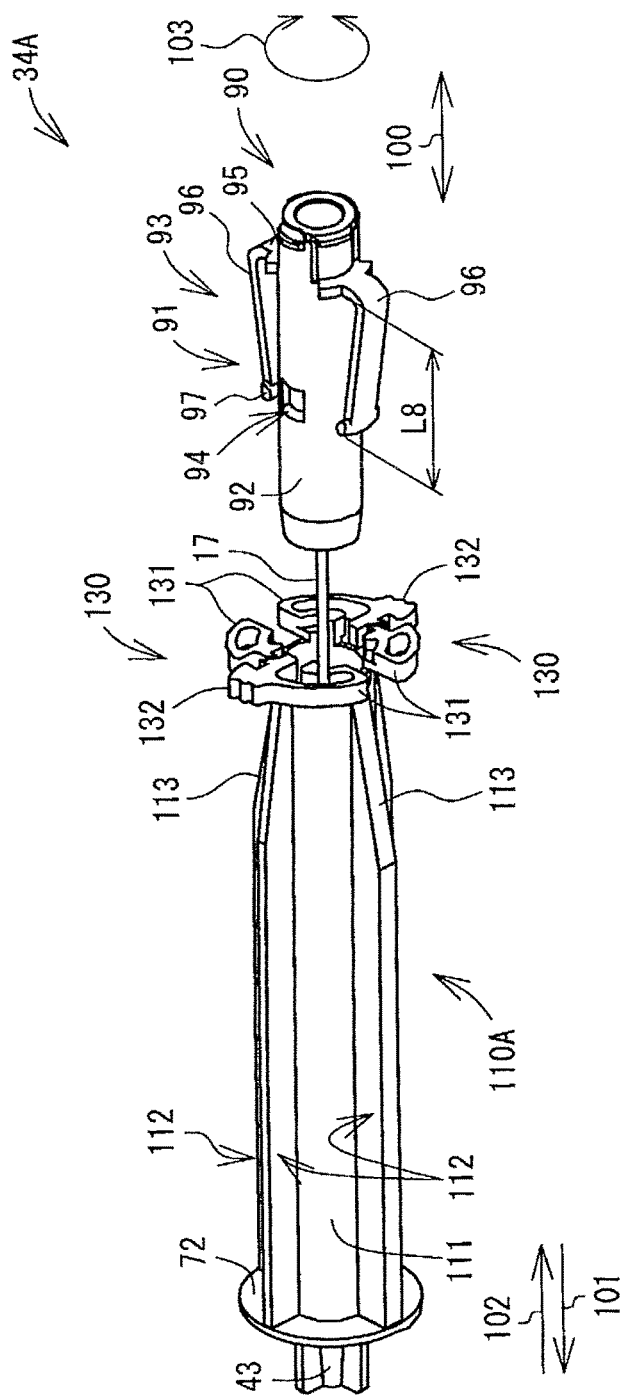
FIG. 22 is an exploded perspective view of a connection device 34A of Modification 3.

This modification describes a connection device 34A illustrated in FIG. 22. In the following description, those having the same configurations of the connection devices 14, 24, and 34 are denoted by the same reference numerals. In more detail, in the connection device 34A according to Modification 3, the configuration of a lock mechanism 130 described later is different from that in the connection device 34 according to Modification 2 and the other configurations are the same as those of the connection device 34 according to Modification 2. Therefore, the following description is given with reference to some of the drawings of Modification 2.

The connection device 34A has a first member 90, a second member 110A, a hollow needle 17, and a hub 42. The first member 90 is a member which holds the hollow needle 17 and the hub 42. The second member 110A is a member which covers a tip 18 of the hollow needle 17.

[First Member 90]

The first member 90 illustrated in FIG. 22 is constituted by a cylinder portion 92 and elastic portions 93 as in Modification 2 and the hub 42 is attached to an opening on a side in the second direction 102 of the cylinder portion 92. The first member 90 is moved relative to the second member 110A in the axial direction 100 in the internal space (equivalent to the second internal space) of the base 111 of the second member 110A as described later. Into through-holes 94 provided at almost the center of the cylinder portion 92 in the axial direction 100, engagement convex portions 133 of the second member 110A are fitted when the connection device 34A is discarded as in Modification 2. Thus, the first member 90 is fixed to the second member 110A. The through-holes 94 are equivalent to the engagement concave portions.

The elastic portion 93 illustrated in FIG. 22 has a flange 95, a projection pieces 96, and a pair of bosses 97 as in Modification 2. As illustrated in FIG. 23(B), the flange 95 abuts on the base 111 of the second member 110A, and restrains relative movement in the axial direction 100 of the first member 90 and the second member 110A.

As illustrated in FIG. 23(A) and FIG. 23(B), the projection pieces 96 slide on inclines 113 of the second member 110A to be elastically bent in the relative movement of the first member 90 and the second member 110A. The bent projection pieces 96 elastically energize the second member 110A in the first direction 101 with respect to the first member 90. As illustrated in FIG. 23(A), the bosses 97 abut on the elastic pieces 131 of the second member 110A, and restrain relative movement in the axial direction 100 of the first member 90 and the second member 110A.

The first member 90 is restrained from the relative movement to the second member 110A by the abutting of the bosses 97 and the elastic pieces 131 on the abutting of the flange 95 on the base 111. Therefore, the moving range to the second member 110A of the first member 90 in the axial direction 100 is within the range of a length L8 (FIG. 22) of the projection pieces 96 in the axial direction 100. The length L8 of the projection pieces 96 is made longer than a thickness T (FIG. 3) of a gasket 35 in such a manner that the tip 18 of the hollow needle 17 can penetrate the gasket 35 (FIG. 3).

[Second Member 110A]

As illustrated in FIG. 22, the second member 110A is a resin molded article of polypropylene or the like having a base 111, four reinforcing ribs 112, a third flange 72, and lock mechanisms 130. The configurations of the base 111, the four reinforcing ribs 112, and the third flange 72 are the same as those of Modification 2.

A pair of lock mechanisms 130 are provided on the end on a side in the second direction 102 of the base 111 facing each other in the radial direction of the base 111. The lock mechanism 130 has the elastic pieces 131, a holding portion 132 provided to the elastic pieces 131, and an engagement convex portion 133 projected from the holding portion 132.

A pair of the elastic piece 131 are provided on both sides of the holding portion 132 in the circumferential direction 103 of the second member 110A. One of the pair of elastic pieces 131 is formed into an almost U shape, which is elastically deformed, and one end thereof is joined to the base 111 and the other end is joined to the holding portion 132. More specifically, the elastic pieces 131 elastically energize the holding portion 132 to the outside in the radial direction of the base 111. The elastic pieces 131 are equivalent to the energizing portion. In contrast thereto, the other one of the pair of elastic pieces 131 is joined only to the base 111 and is separated from the holding portion 132. More specifically, the holding portion 132 is elastically supported by only one of the pair of elastic pieces 131.

Figure 23:
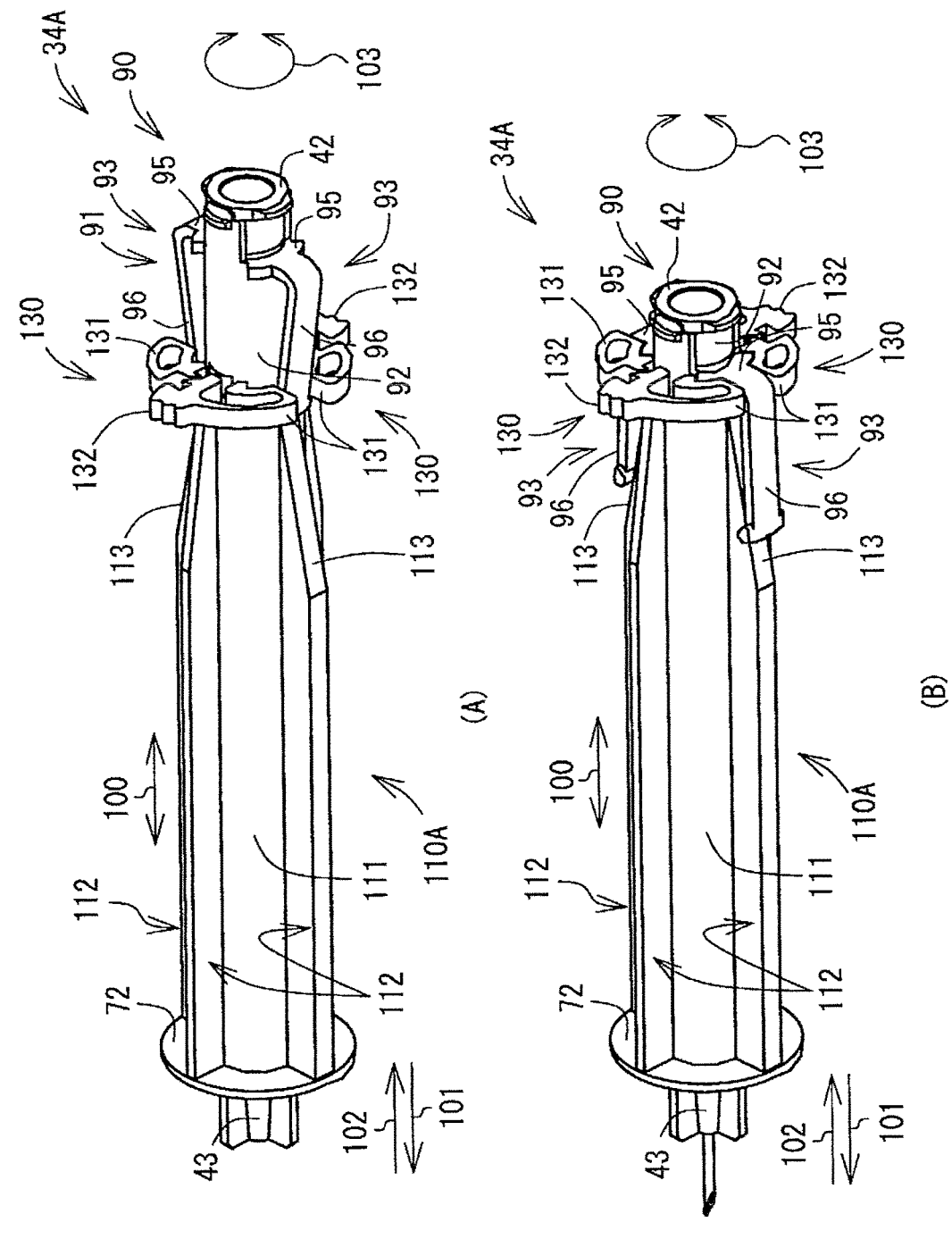
FIG. 23 includes views explaining an operation of the connection device 24A of Modification 3.
Figure 24:
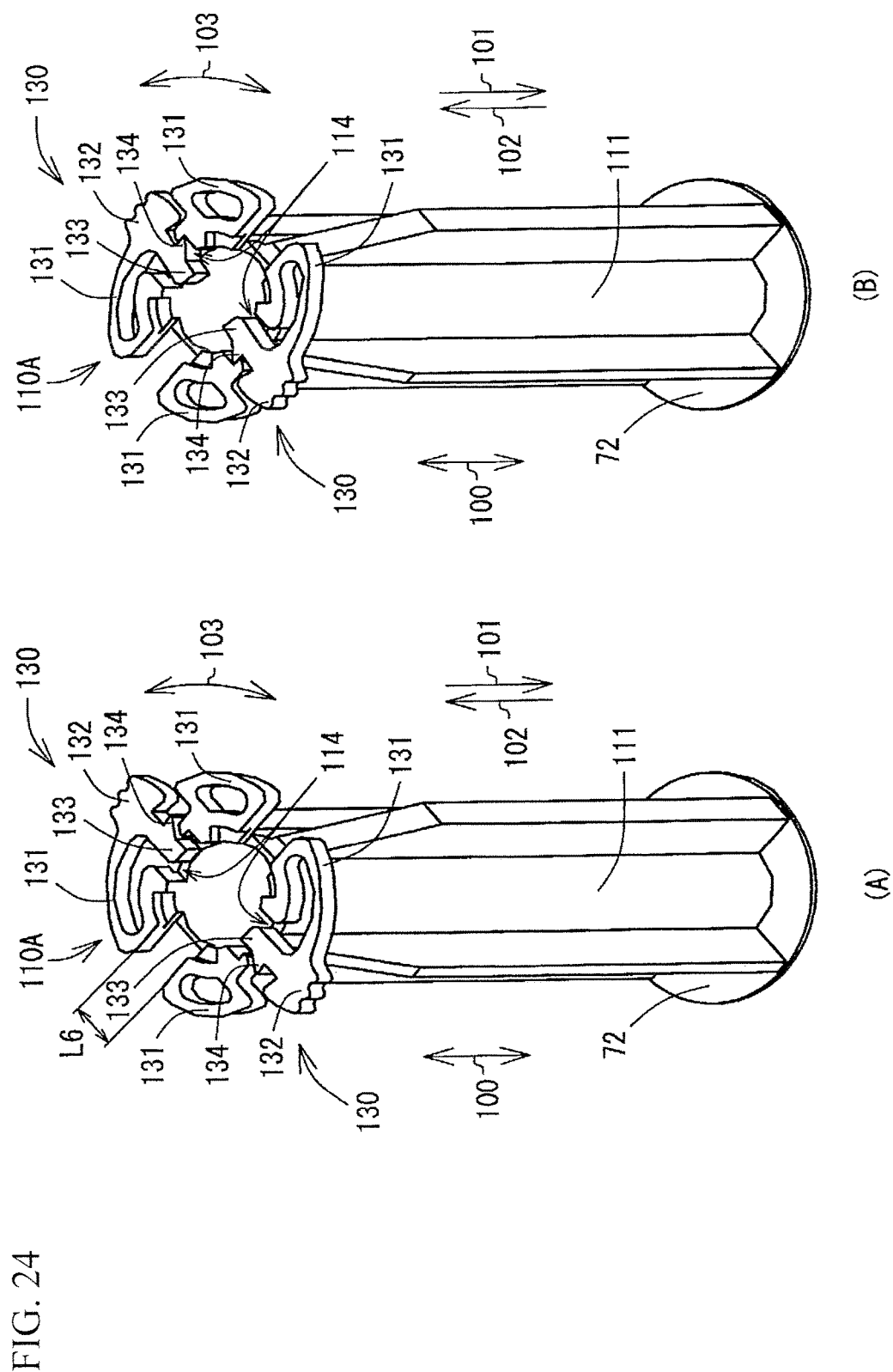
FIG. 24 includes views explaining an operation of lock mechanism 130 of Modification 3.

The elastic pieces 131 of one lock mechanism 130 and the elastic pieces 131 of the other lock mechanism 130 are separated from each other only by a distance L6 (FIG. 24(A)) in the radial direction of the base 111. The distance L6 is made longer than a width W2 (FIG. 15) of the projection pieces 96 of the first member 90. As illustrated in FIG. 23, the projection pieces 96 are extended to inclines 113 through between the pair of elastic pieces 131, and abut on the inclines 113 at the tip. The distance L6 is made shorter than a distance L7 (FIG. 15) between the tips of projections of the pair of bosses 97 of the first member 90. As illustrated in FIG. 23(A), when the first member 90 and the second member 110A are relatively moved in the axial direction 100, the bosses 97 abut on the elastic pieces 131, so that the relative movement of the first member 90 and the second member 110A is restrained.

As illustrated in FIG. 22, the holding portion 132 is provided in the middle of the pair of elastic pieces 131. The holding portion 132 has a plate shape along the outer circumferential surface of the base 111. The holding portion 132 supports the engagement convex portion 133 facing the through-hole 94 of the first member 90 in the state where the second member 110A was attached to the first member 90. The pair of holding portions 132 of the pair of lock mechanisms 130 face each other in the radial direction of the base 111. When the pair of holding portions 132 are held by a user, the elastic piece 131 are elastically deformed, so that the holding portions 132 abut on the outer circumferential surface of the base 111 (FIG. 24(B)).

The engagement convex portions 133 are projected from the holding portions 132 toward the central portion of the base 111. A pair of notches 114 which are notched from the end surface on a side in the second direction 102 are provided in the base 111, and the tips of the engagement convex portions 133 are located in this notches 114. The edge of the notch 114 in Modification 3 serves as an end portion of the other one of the pair of elastic pieces 131 (i.e., the elastic piece 131 which does not support the holding portion 132). When the holding portions 132 are pressed by a user, and the holding portions 132 abut on the outer circumferential surface of the base 11, the tips of the engagement convex portions 133 are projected to the inside of the inner circumferential surface of the base 111 (FIG. 24(B)), and are fitted into the through-holes 94 of the first member 90 at the first position (FIGS. 25(B), 25(D)).

As illustrated in FIG. 22, projections 134 in a triangular shape as viewed in plane are projected in the circumferential direction 103 from one side surface of the engagement convex portions 133 in the circumferential direction 103. In more detail, the projections 134 are projected from the engagement convex portions 133 toward the other one of the pair of elastic pieces 13 (i.e., the elastic piece 131 which does not support the holding portion 132). When the holding portions 132 are held by a user, and the holding portions 132 abut on the outer circumferential surface of the base 111

(FIG. 24(B)), the projections 134 are caught in the edges of the notches 114 of the base 111 (i.e., engaged with the other elastic piece 131), and are latched by the base 111. Thus, the first member 90 is fixed to the second member 110A. The projections 134 are equivalent to the lock portion.

Figure 25:
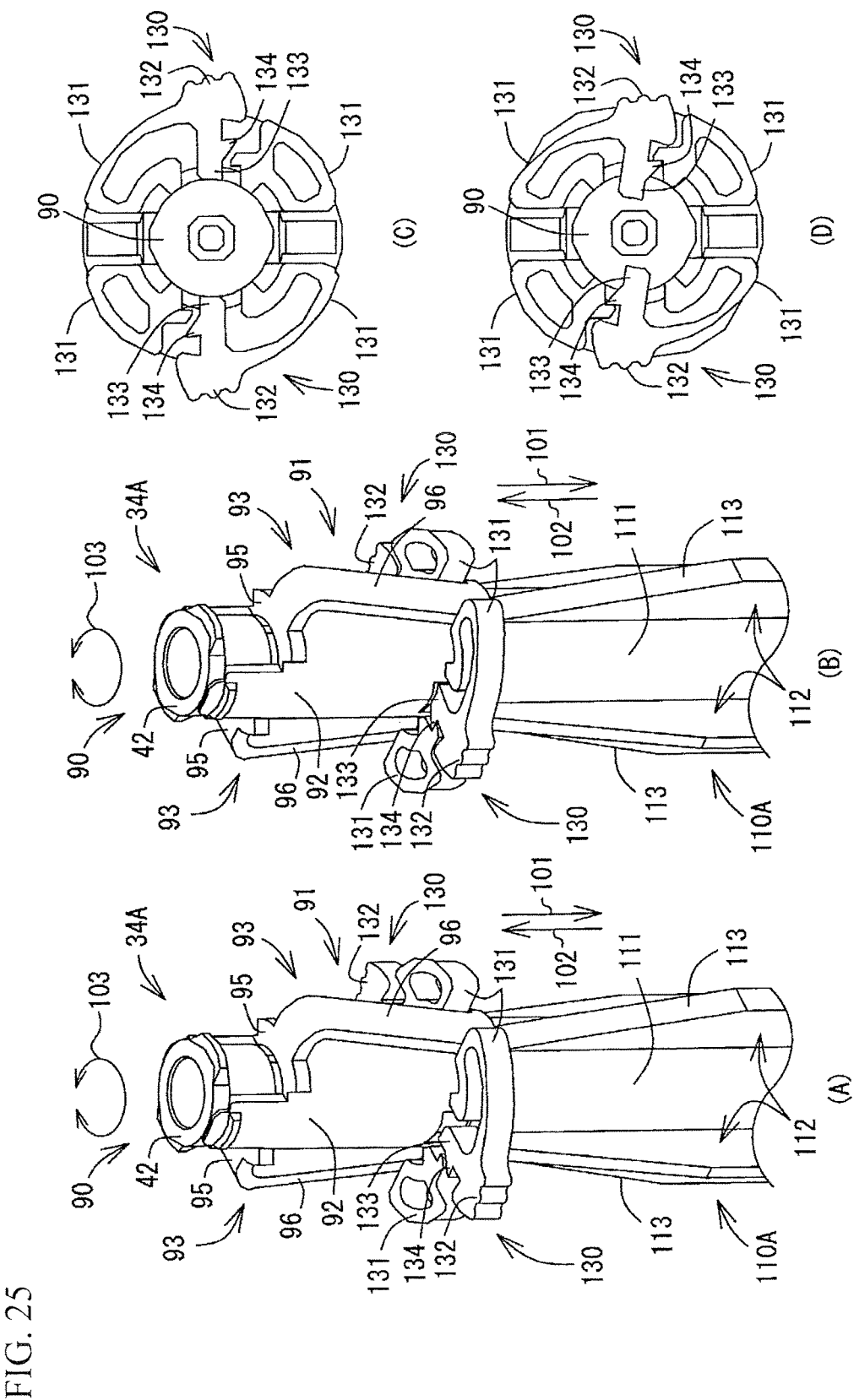
FIG. 25 includes views explaining an operation when a first member 90 is fixed to a second member 110A in Modification 3.

An operation when discarding the connection device 34A is described with reference to FIG. 25. After a series of operations for obtaining PRP (FIG. 9) are completed, the pair of holding portions 132 are held by a user. Thus, the lock mechanisms 130 are moved to a position illustrated in FIGS. 25(B) and 25(D) from a position illustrated in FIGS. 25(A) and 25(C) by the elastic deformation of the elastic pieces 131. Thus, the engagement convex portions 133 of the lock mechanisms 130 are fitted into the through-holes 94 of the first member 90, and the projections 134 are caught in the edges of the notches 114 (FIG. 24(B)). In more detail, the projections 134 and the other elastic pieces 131 are engaged with each other. Thus, the first member 90 is fixed to the second member 110A in the state where the second member 110A accommodates the tip 18 of the hollow needle 17. The connection device 34A is discarded in this state.

[Effects]

In this modification, since the hollow needle 17 is provided in the connection device 34A, it is not necessary to pass the hollow needle 17 into the connection device 34A. Moreover, the tip 18 of the hollow needle 17 is in the second member 60 and abuts on the gasket 35 until the connection device 34A is inserted into the internal space of the syringe barrel 20 and abuts on the gasket 35. The tip 18 of the hollow needle 17 is in the syringe barrel 20 after the connection device 34A abuts on the gasket 35, and is further pressed into the internal space of the syringe barrel 20. Therefore, in a series of operations for obtaining PRP, a user can be prevented from accidentally pricking the user with the hollow needle 17.

Moreover, in this modification, since the first member 90 can be fixed to the second member 110A by the lock mechanisms 130 when discarding the connection device 34A, a possibility that the tip 18 of the hollow needle 17 is accidentally exposed in the discarded connection device 34A is reduced.

[Other Modifications]

The embodiment and the modifications described above describe the examples in which the cylinder portion 61 and the elastic portions 63, the cylinder portion 81 and the elastic pieces 82, and the cylinder portion 92 and the elastic portions 93 are integrally molded with resin materials. However, a plate spring may be provided in place of the elastic portions 63, the elastic pieces 82, or the elastic portions 93. The plate spring is formed into the same shape as that of the elastic portions 63, the elastic pieces 82, or the elastic portions 93, and is stuck to the cylinder portion 61, the cylinder portion 81, or the cylinder portion 92.

The embodiment and the modifications described above describe the examples in which the hub 42 is attached to the first members 40, 70, and 90. However, a connection portion attached to and detached from the port 21 of the syringe barrel 20 may be directly formed in the first members 40, 70, and 90 by molding in place of the hub 42. Moreover, a hub having a screw hole into which the port 21 is screwed may be used in place of the hub 42 into which the port 21 is press-fitted.

REFERENCE SIGNS LIST

10 Blood component separation apparatus
11, 12, 13 Syringe
14, 24, 34, 34A Connection device
16 Cap
17 Hollow needle
20 Syringe barrel
21 Port
25 Plunger
35 Gasket
40, 70, 90 First member
42 Hub
49, 113 Inclines
51 Concave portion (engagement portion)
60, 80, 110, 110A Second member
64, 96 Projection piece
73 Long hole
76 Convex portion (engagement portion)
82 Elastic piece
94 Through-hole (engagement concave portion)
120, 130 Lock mechanism
121, 132 Elastic piece (energizing portion)
122, 132 Holding portion
123, 133 Engagement projection portion
124, 134 Projection (lock portion)
PRP Platelet rich plasma

The invention claimed is:

1. A connection device, comprising:
a first member in a tube shape having a first internal space which extends in a longitudinal direction and opens to both end sides;
a hollow needle having a hub connectable to a port of a syringe provided on a base end side of the first member and extending from the hub to a tip side in the first internal space of the first member; and
a second member comprising a base portion, a small diameter portion, a flange, and a plurality of longitudinally-extending ribs, the base portion having a second internal space which extends in the longitudinal direction and opens to both end sides, the second member being provided on a tip side of the first member by continuously connecting the second internal space to the first internal space, and which can move relative to the first member in the longitudinal direction, and
wherein the small diameter portion is located at a first end side of the second member furthest from said base end side of said first member, said flange being located toward said first end adjacent to said small diameter portion,
wherein each one rib of said plurality of longitudinally-extending ribs extends from said flange toward a second end of said second member and projects radially from an outer circumference of said base portion,
wherein said each one rib has a first portion extending axially from the flange and having a constant radial height from said tube portion,
wherein said each one rib has a second portion located toward said second end of said second member, said second portion extending axially from said first portion toward said second end and projecting radially at a varying height to form a tapered incline of decreasing radial height from said first portion toward said second end,
wherein a location along said each one rib where said first portion ends and said second portion begins is located closer to said second end of the second member than said first end,
wherein the second member can move to a first position where a tip of the hollow needle is accommodated in the second internal space and a second position where the tip of the hollow needle is exposed from the second internal space and is elastically energized to a first position side relative to the first member, wherein the first member is provided with lock mechanisms which fix the second member in such a manner that the second member does not move from the first position, wherein the first member is provided with a plurality of projection pieces, each one projection piece, among said plurality of projection pieces, extending in the longitudinal direction toward said tapered incline of a corresponding rib of said plurality of longitudinally extending ribs, and being elastically deformed in such a manner as to outwardly spread by abutting of the tip side on said tapered incline of said corresponding rib, and wherein the second member is elastically energized to the first position side by a restoring force of the elastically deformed projection pieces.

2. A blood component separation apparatus, comprising:
the connection device according to any claim 1;
a first syringe having a first syringe barrel into which is inserted the small diameter portion, the flange, and a partial length portion of said first portion of each one of said plurality of longitudinally-extending ribs of said second member,
the first syringe having a first gasket which is moved back and forth in the first syringe barrel, and a plunger which is attached to and detached from the first gasket;
a cap which seals a first port of the first syringe barrel; and
a second syringe having a second port to which the connection device is attached,
wherein when the second member of the connection device reaches a second position, the hollow needle exposed from the second internal space can penetrate the first gasket, and
wherein said first portion of said each one rib is configured to have said constant radial height thereby radially fitting within a diameter of said first syringe barrel.

3. The connection device according to claim 1, wherein the lock mechanisms are configured to lock the second member into said first position after use of the hollow needle, the lock mechanisms being located at said second end of said second member.

4. The connection device according to claim 3, wherein the lock mechanisms comprise a plurality of elastic pieces, and wherein said one projection piece extends between a pair of said elastic pieces to abut the tapered incline of a corresponding rib when the second member is moved from the first position to the second position.

5. A connection device, comprising:
a first member in a tube shape having a first internal space which extends in a longitudinal direction and opens to both end sides;
a hollow needle having a hub connectable to a port of a syringe provided on a base end side of the first member and extending from the hub to a tip side in the first internal space of the first member; and
a second member which has a second internal space which extends in the longitudinal direction and opens to both end sides, which is provided on a tip side of the first member by continuously connecting the second internal space to the first internal space, and which can move relative to the first member in the longitudinal direction, and wherein the second member can move to a first position where a tip of the hollow needle is accommodated in the second internal space and a second position where the tip of the hollow needle is exposed from the second internal space and is elastically energized to a first position side relative to the first member, wherein the first member is provided with lock mechanisms which fix the second member in such a manner that the second member does not move from the first position, wherein tapered inclines which outwardly spread toward a tip side are provided on an outer wall on a base end side of the second member, wherein the first member is provided with projection pieces which are extended toward the inclines in the longitudinal direction and can be elastically deformed in such a manner as to outwardly spread by abutting of the tip side on the inclines, wherein the second member is elastically energized to the first position side by a restoring force of the elastically deformed projection pieces, wherein engagement concave portions are provided in an outer wall of the first member, wherein the second member is provided with engagement convex portions which can engage with the engagement concave portions, energizing portions which elastically energize the engagement convex portions to a side where the engagement convex portions do not engage with the engagement concave portions, and lock portions which fix the engagement convex portions to a position where the engagement convex portions engage with the engagement concave portions against energization force caused by the energizing portions, and wherein the second member is fixed to the first position by engagement of the engagement concave portions with the engagement convex portions.

6. The connection device according to claim 5, wherein the second member is provided with holding portions which support the engagement convex portions facing the engagement concave portions,
a pair of the energizing portions are provided on both sides of the holding portions and elastically support the holding portions by the pair of energizing portions, and
the lock portions are projected toward both of the pair of energizing portions from the engagement convex portions and engage with both of the pair of energizing portions to thereby fix the engagement convex portions to the position where the engagement convex portions engage with the engagement concave portions.

7. The connection device according to claim 5, wherein the second member is provided with holding portions which support the engagement convex portions facing the engagement concave portions,
a pair of the energizing portions are provided on both sides of the holding portions and elastically support the holding portions by one of the pair of energizing portions, and
the lock portions are projected toward the other one of the pair of energizing portions from the engagement convex portions and engage with the other one of the pair of energizing portions to thereby fix the engagement convex portions to the position where the engagement convex portions engage with the engagement concave portions.

8. A blood component separation apparatus, comprising:
the connection device according to any one of claims 5, 6, and 7;
a first syringe having a first syringe barrel into which a tip side of the connection device is inserted, a first gasket which is moved back and forth in the first syringe barrel, and a plunger which is attached to and detached from the first gasket;
a cap which seals a first port of the first syringe barrel; and
a second syringe having a second port to which the connection device is attached,
wherein when the second member of the connection device reaches a second position, the hollow needle exposed from the second internal space can penetrate the first gasket.

9. A connection device, comprising:
a first member in a tube shape having a first internal space which extends in a longitudinal direction and opens to both end sides;
a hollow needle having a hub connectable to a port of a syringe provided on a base end side of the first member and extending from the hub to a tip side in the first internal space of the first member; and
a second member which has a second internal space which extends in the longitudinal direction and opens to both end sides, which is provided on a tip side of the first member by continuously connecting the second internal space to the first internal space, and which can move relative to the first member in the longitudinal direction, and
wherein the second member can move to a first position where a tip of the hollow needle is accommodated in the second internal space and a second position where the tip of the hollow needle is exposed from the second internal space and is elastically energized to a first position side relative to the first member,
wherein the first member is provided with lock mechanisms which fix the second member in such a manner that the second member does not move from the first position,
wherein tapered inclines which outwardly spread toward a tip side are provided on an outer wall on a base end side of the second member,
wherein the first member is provided with projection pieces which are extended toward the inclines in the longitudinal direction and can be elastically deformed in such a manner as to outwardly spread by abutting of the tip side on the inclines,
wherein the second member is elastically energized to the first position side by a restoring force of the elastically deformed projection pieces,
wherein the lock mechanisms comprise a plurality of elastic pieces located at an end of said second member away from said tip side of said hollow needle, and
wherein a projection piece among said projection pieces extends between a pair of said elastic pieces to abut the tapered incline of a corresponding rib when the second member is moved from the first position to the second position.

10. A connection device, comprising:
a first member in a tube shape having a first internal space which extends in a longitudinal direction and opens to both end sides;
a hollow needle having a hub connectable to a port of a syringe provided on a base end side of the first member and extending from the hub to a tip side in the first internal space of the first member; and
a second member which has a second internal space which extends in the longitudinal direction and opens to both end sides, which is provided on a tip side of the first member by continuously connecting the second internal space to the first internal space, and which can move relative to the first member in the longitudinal direction;
wherein the second member can move to a first position where a tip of the hollow needle is accommodated in the second internal space and a second position where the tip of the hollow needle is exposed from the second internal space and is elastically energized to the first position relative to the first member;
wherein the first member comprises an elastic portion having a flange;
wherein a first projection piece projects from the flange;
wherein a first boss extends in a circumferential direction at a tip end of the first projection piece;
wherein the second member comprises a first elastic piece and a base; and
wherein the first member is restrained from moving relative to the second member by the first boss while the first boss abuts the first elastic piece of the second member and the flange abuts the base of the second member.

11. The connection device according to claim 10, wherein a second projection piece projects from the flange; wherein a second boss extends in a circumferential direction at a tip end of the second projection piece; wherein the second member further comprises a second elastic piece; and
wherein the first member is restrained from moving relative to the second member by the first boss and second boss while the first boss abuts the first elastic piece of the second member, the second boss abuts the second elastic piece of the second member and the flange abuts the base of the second member.

* * * * *